United States Patent [19]
Stemmer et al.

[11] Patent Number: 5,834,252
[45] Date of Patent: Nov. 10, 1998

[54] END-COMPLEMENTARY POLYMERASE REACTION

[75] Inventors: Willem Peter Christiaan Stemmer, Los Gatos, Calif.; Robert J. Lipshutz, Palo Alto, Calif.

[73] Assignee: Glaxo Group Limited, Middlesex, England

[21] Appl. No.: 425,684

[22] Filed: Apr. 18, 1995

[51] Int. Cl.[6] .......................... C12P 19/34; C07H 21/04; C12N 9/14

[52] U.S. Cl. .................. 435/91.1; 435/91.2; 435/91.52; 435/195; 536/24.3

[58] Field of Search ................... 435/91.2, 91.1, 435/91.52, 195; 536/24.3

[56] References Cited

U.S. PATENT DOCUMENTS

| | | |
|---|---|---|
| 4,458,066 | 7/1984 | Caruthers et al. . |
| 4,683,195 | 7/1987 | Mullis et al. . |
| 4,683,202 | 7/1987 | Mullis . |
| 4,800,159 | 1/1989 | Mullis et al. . |
| 4,965,188 | 10/1990 | Mullis et al. . |
| 5,066,584 | 11/1991 | Gyllensten et al. . |
| 5,118,604 | 6/1992 | Weissman et al. ................. 435/6 |
| 5,188,604 | 6/1992 | Weissman et al. . |
| 5,279,952 | 1/1994 | Wu . |
| 5,286,632 | 2/1994 | Jones . |
| 5,340,728 | 8/1994 | Grosz et al. . |

FOREIGN PATENT DOCUMENTS

| | | | |
|---|---|---|---|
| WO 96/05296 | 2/1996 | WIPO | C12N 15/10 |

OTHER PUBLICATIONS

Suzuki, K., et al., "In Vivo Ligation of Linear DNA Molecules to Cirvcular Forms in the Yeast Saccharomyces Cerevisiae", *Journal of Bacteriology*, vol. 155, No. 2, pp. 747–754, Aug. 1983.

White, Michael J., et al., "Concatemer Chain Reaction: A Tag DNA Polymerase–Mediated Mechanism for Generating Long Tandemly Repetitive DNA Sequences", *Analytical Biochemistry*, vol. 199, pp. 184–190, 1991.

Horton, Robert M., et al., "Engineering Hybrid Genes without the Use of Restriction Enzymes: Gene Splicing by Overlap Extension", *Gene*, vol. 77, pp. 61–68, 1989.

Jones, Douglas H., et al., "A Rapid Method for Site–Specific Mutagenesis and Directional Subcloning by Using the Polymerase Chain Reaction to Generate Recombinant Circles", *BioTechniques*, vol. 8, No. 2, pp. 178–183, 1990.

Oliner, Jonathan D., et al., "In Vivo Cloning of PCR Products in *E.coli*", *Nucl. Acids Res.*, vol. 21, No. 22, pp. 5192–5197, 1993.

Silver, Jonathan, et al., "Novel Use of Polymerase Chain Reaction to Amplify Cellular DNA Adjacent to an Integrated Provirus", *J. Virol.*, vol. 63, No. 5, pp. 1924–1928, May 1989.

Stemmer, Willem P. C., "Rapid Evolution of a Protein in vitro by DNA Shuffling", *Nature*, vol. 370, pp. 389–391, 04 Aug. 1994.

(List continued on next page.)

*Primary Examiner*—W. Gary Jones
*Assistant Examiner*—Joyce Tung
*Attorney, Agent, or Firm*—Townsend and Townsend & Crew

[57] ABSTRACT

The present invention is directed to a process for amplifying and detecting any target nucleic acid sequence contained in a nucleic acid or mixture thereof and for assembling large polynucleotides from component polynucleotides, each involving generating concatemers formed by PCR amplification of overlapping fragments.

8 Claims, 13 Drawing Sheets

OTHER PUBLICATIONS

Triglia, Tony et al., "A Procedure for In Vitro Amplification of DNA Segments that Lie Outside the Boundaries of Known Sequences", *Nucl. Acids Res.*, vol. 16, No. 16, p. 8186, 1988.

Vallette, Francois, et al., "Construction of Mutant and Chimeric Genes Using the Polymerase Chain Reaction", *Nucl. Acids Res.*, vol. 17, No. 2, pp. 723–733, 1989.

Katsuyuki et al. In Vivo Ligation of Linear DNA Molecules to Circular Forms in the Yeast *Saccharomyces cerevisiae* 1983 J. of Bacteriology pp. 747–754.

White et al. Concatemer Chain Reaction: A Taq DNA Polymerase–Mediated Mechanism for Generating Long Tandemly Repetitive DNA Sequences, 1991, Analytical Biochemistry pp. 184–190.

① INITIAL DNA
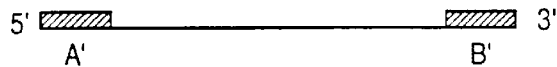
INITIAL PRIMER
② ANNEALING
③ EXTENSION
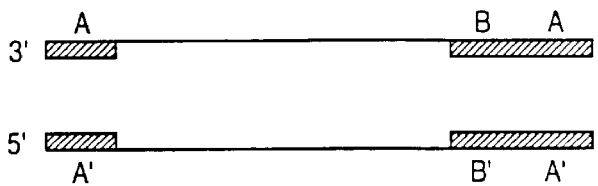
④ MELT AND REANNEAL TO GET 6 POSSIBLE HYBRIDS
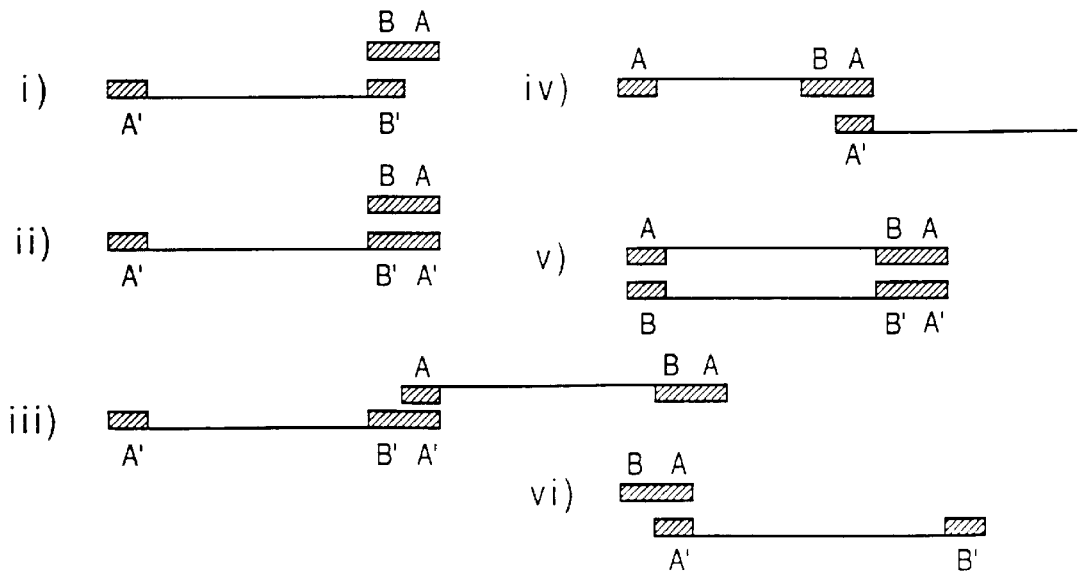
FIG. 1A ④ EXTEND
ONLY HYBRIDS i, ii, iii EXTEND
⑤ MELT
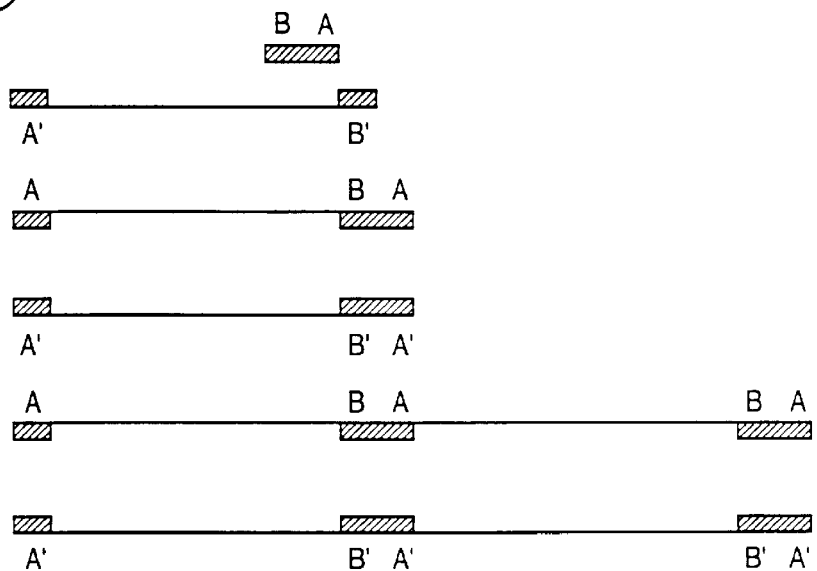
REANNEALING GIVES THE FOLLOWING POSSIBLE
EXTENDIBLE HYBRIDS
    i, ii, iii FROM STEP 4
AND
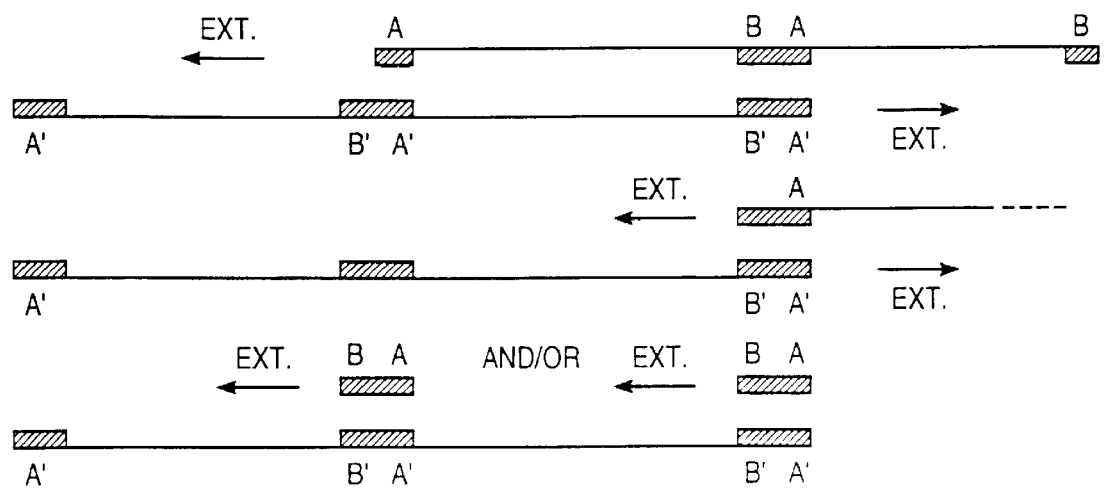
FIG. 1B

| R1  | CTC ACG TTA AGG GAT TTT GGT CAT GAG ATT ATC AAA AAG G |
|-----|---|
| R2  | ATC TTC ACC TAG ATC CTT TTA AAT TAA AAA TGA AGT TTT A |
| R3  | AAT CAA TCT AAA GTA TAT ATG AGG CCT GAC AGG CCG GTC T |
| R4  | GAC AGT TAC CAA TGC TTA ATC AGT GAG GCA CCT ATC TCA G |
| R5  | CGA TCT GTC TAT TTC GTT CAT CCA TGG TTG CCT GAC TCC C |
| R6  | CGT CGT GTA GAT AAC TAC GAT ACG GGA GGG CTT ACC ATC T |
| R7  | GGC CCC AGT GCT GCA ATG ATA CCG CGA GAC CCA CGC TCA C |
| R8  | CGG CTC CAG ATT TAT CAG CAA TAA ACC AGC CAG CTG GAA G |
| R9  | GGC CGA GCG CAG AAG TGG TCC TGC AAC TTT ATC CGC CTC C |
| R10 | ATC CAG TCT ATT AAT TGT TGC CGG GAA GCT AGA GTA AGT A |
| R11 | GTT CGC CAG TTA ATA GTT TGC GCA ACG TTG TTG CCA TGG C |
| R12 | TAC AGG CAT CGT GGT GTC ACG CTC GTC GTT TGG AAT GGC T |
| R13 | TCA TTC AGC TCC GGT TCC CAA CGA TCA AGG CGA GTT ACA T |
| R14 | GAT CCC CCA TGT TGT GCA AAA AAG CGG TTA GCT CCT TCG G |
| R15 | TCC TCC GAT CGT TGT CAG AAG TAA GTT GGC TGC AGT GTT A |
| R16 | TCA CTC ATG GTT ATG GCA GCA CTG CAT AAT TCT CTT ACT G |
| R17 | TCA TGC CAT CCG TAA GAT GCT TTT CTG TGA CTG GTG AGT A |
| R18 | CTC AAC CAA GTC ATT CTG AGA ATA GTG TAT GCG GCG ACC G |
| R19 | AGT TGC TCT TGC CCG GCG TCA ATA CGG GAT AAT ACC GCG C |
| R20 | CAC ATA GCA GAA CTT TAA AAG TGC TCA TCA TTG GAA AAC G |
| R21 | TCC TTC GGG GCG AAA ACT CTC AAG GAT CTT ACC GCT GTT G |
| R22 | AGA TCC AGT TCG ATG TAA CCC ACT CGT GCA CCC AAC TGA T |
| R23 | CTT CAG CAT CTT TTA CTT TCA CCA GCG TTT CTG GGT GAG C |
| R24 | AAA AAC AGG AAG GCA AAA TGC CGC AAA AAA GGG AAT AAG G |
| R25 | GCG ACA CGG AAA TGT TGA ATA CTC ATA CTC TTC CTT TTT C |
| R26 | AAT ATT ATT GAA GCA TTT ATC AGT GTT ATT GTC TCA TGA G |
| R27 | CGG ATA CAT ATT TGA ATG TAT TTA GGC CAT GGT GGC CAA A |
| R28 | AAT AAA CAA ATA GGG GTT CCG CGC ACA TTT CCC CGA AAA G |

FIG. 5A

| | | | | | | | | | | | | |
|---|---|---|---|---|---|---|---|---|---|---|---|---|
| 1  | TTC | TTA | GAC | GTC | AGG | TGG | CAC | TTT | TCG | GGG | AAA | TGT | GCG | C |
| 2  | GGA | ACC | CCT | ATT | TGT | TTA | TTT | TTG | GCC | ACC | ATG | GCC | TAA | A |
| 3  | TAC | ATT | CAA | ATA | TGT | ATC | CGC | TCA | TGA | GAC | AAT | AAC | CCT | G |
| 4  | ATA | AAT | GCT | TCA | ATA | ATA | TTG | AAA | AAG | GAA | GAG | TAT | GAG | T |
| 5  | ATT | CAA | CAT | TTC | CGT | GTC | GCC | CTT | ATT | CCC | TTT | TTT | GCG | G |
| 6  | CAT | TTT | GCC | TTC | CTG | TTT | TTG | CTC | ACC | CAG | AAA | CGC | TGG | T |
| 7  | GAA | AGT | AAA | AGA | TGC | TGA | AGA | TCA | GTT | GGG | TGC | ACG | AGT | G |
| 8  | GGT | TAC | ATC | GAA | CTG | GAT | CTC | AAC | AGC | GGT | AAG | ATC | CTT | G |
| 9  | AGA | GTT | TTC | GCC | CCG | AAG | AAC | GTT | TTC | CAA | TGA | TGA | GCA | C |
| 10 | TTT | TAA | AGT | TCT | GCT | ATG | TGG | CGC | GGT | ATT | ATC | CCG | TAT | T |
| 11 | GAC | GCC | GGG | CAA | GAG | CAA | CTC | GGT | CGC | CGC | ATA | CAC | TAT | T |
| 12 | CTC | AGA | ATG | ACT | TGG | TTG | AGT | ACT | CAC | CAG | TCA | CAG | AAA | A |
| 13 | GCA | TCT | TAC | GGA | TGG | CAT | GAC | AGT | AAG | AGA | ATT | ATG | CAG | T |
| 14 | GCT | GCC | ATA | ACC | ATG | AGT | GAT | AAC | ACT | GCA | GCC | AAC | TTA | C |
| 15 | TTC | TGA | CAA | CGA | TCG | GAG | GAC | CGA | AGG | AGC | TAA | CCG | CTT | T |
| 16 | TTT | GCA | CAA | CAT | GGG | GGA | TCA | TGT | AAC | TCG | CCT | TGA | TCG | T |
| 17 | TGG | GAA | CCG | GAG | CTG | AAT | GAA | GCC | ATT | CCA | AAC | GAC | GAG | C |
| 18 | GTG | ACA | CCA | CGA | TGC | CTG | TAG | CCA | TGG | CAA | CAA | CGT | TGC | G |
| 19 | CAA | ACT | ATT | AAC | TGG | CGA | ACT | ACT | TAC | TCT | AGC | TTC | CCG | G |
| 20 | CAA | CAA | TTA | ATA | GAC | TGG | ATG | GAG | GCG | GAT | AAA | GTT | GCA | G |
| 21 | GAC | CAC | TTC | TGC | GCT | CGG | CCC | TTC | CAG | CTG | GCT | GGT | TTA | T |
| 22 | TGC | TGA | TAA | ATC | TGG | AGC | CGG | TGA | GCG | TGG | GTC | TCG | CGG | T |
| 23 | ATC | ATT | GCA | GCA | CTG | GGG | CCA | GAT | GGT | AAG | CCC | TCC | CGT | A |
| 24 | TCG | TAG | TTA | TCT | ACA | CGA | CGG | GGA | GTC | AGG | CAA | CCA | TGG | A |
| 25 | TGA | ACG | AAA | TAG | ACA | GAT | CGC | TGA | GAT | AGG | TGC | CTC | ACT | G |
| 26 | ATT | AAG | CAT | TGG | TAA | CTG | TCA | GAC | CGG | CCT | GTC | AGG | CCT | C |
| 27 | ATA | TAT | ACT | TTA | GAT | TGA | TTT | AAA | ACT | TCA | TTT | TTA | ATT | T |
| 28 | AAA | AGG | ATC | TAG | GTG | AAG | ATC | CTT | TTT | GAT | AAT | CTC | ATG | A |

FIG. 5B

{58F}
GGAAAACCCTGGCGTTACCCAACTTAATCGCCTTGCAGCA
{59F}
CATCCCCCTTTCGCCAGCTGGCGTAATAGCGAAGAGGCCC
{60F}
GCACCGATCGCCCTTCCCAACAGTTGCGTAGCCTGAATGG
{61F}
CGAATGGCGCCTGATGCGGTATTTTCTCCTTACGCATCTG
{62F}
TGCGGTATTTCACACCGCATATGGTGCACTCTCAGTACAA
{63F}
TCTGCTCTGATGCCGCATAGTTAAGCCAGCCCCGACACCC
{64F}
GCCAACACCCGCTGACGCGCCCTGACGGGCTTGTCTGCTC
{65F}
CCGGCATCCGCTTACAGACAAGCTGTGACCGTCTCCGGGA
{66F}
GCTGCATGTGTCAGAGGTTTTCACCGTCATCACCGAAACG
{30R}
CGAGGCCCTTTCGTCTCGCGCGTTTCGGTGATGACGGTGA
{31R}
AAACCTCTGACACATGCAGCTCCGGAGACGGTCACAGCT
{32R}
TGTCTGAAGCGGATGCCGGGAGCAGACAAGCCCGTCAGG
{33R}
GCGCGTCAGCGGGTGTTGGCGGGTGTCGGGGCTGGCTTAA
{34R}
CTATGCGGCATCAGAGCAGATTGTACTGAGAGTGCACCAT
{35R}
ATGCGGTGTGAAATACCGCCAGATGCGTAAGGAGAAAAT
{36R}
ACCGCATCAGGCGCCATTCGCCATTCAGGCTACGCAACTG
{37R}
TTGGGAAGGGCGATCGGTGCGGGCCTCTTCGCTATTACGC
{38R}
CAGCTGGCGAAAGGGGGATGTGCTGCAAGGCGATTAAGTT
{39R}
GGGTAACGCCAGGGTTTTCCCAGTCACGACGTTGTAAAAC
{40R}
GACGGCCAGTGCCAAGCTTGCATGCCTGCAGGTCGACTCT
{41R}
AGAGGATCCCCGGGTACCGGAGCTCGAATTCGTAATCATGG
{42R}
TCATAGCTGTTTCCTGTGTGAAATTGTTATCCGCTACAA
{43R}
TTCCACACAACATACGAGCCGGAAGCATAAAGTGTAAAGC
{44R}
CTGGGGTGCCTAATGAGTGAGCTAACTCACATTAATTGCG

FIG. 5C

{45R}
TTGCGCTCACTGCCCGCTTTCCAGTCGGGAAACCTGTCGT
{46R}
GCCAGCTGCATTAATGAATCGGCCAACGCGCGGGGAGAGG
{47R}
CGGTTTGCGTATTGGGCGCTCTTCCGCTTCCTCGCTCACT
{48R}
GACTCGCTGCGCTCGGTCGTTCGGCTGCGGCGAGCGGTAT
{48R}
GACTCGCTGCGCTCGGTCGTTCGGCTGCGGCGAGCGGTAT
{49R}
CAGCTCACTCAAAGGCGGTAATACGGTTATCCACAGAATC
{50R}
AGGGGATAACGCAGGAAAGAACATGTGAGCAAAAGGCCAG
{51R}
CAAAAGGCCAGGAACCGTAAAAAGGCCGCGTTGCTGGCGT
{52R}
TTTTCCATAGGCTCCGCCCCCTGACGAGCATCACAAAAA
{53R}
TCGACGCTCAAGTCAGAGGTGGCGAAACCCGACAGGACTA
{54R}
TAAAGATACCAGGCGTTTCCCCCTGGAAGCTCCCTCGTGC
{55R}
GCTCTCCTGTTCCGACCCTGCCGCTTACCGGATACCTGTC
{56R}
CGCCTTTCTCCCTTCGGGAAGCGTGGCGCTTTCTCAATGC
{57R}
TCACGCTGTAGGTATCTCAGTTCGGTGTAGGTCGTTCGCT
{58R}
CCAAGCTGGGCTGTGTGCACGAACCCCCCGTTCAGCCCGA
{59R}
CCGCTGCGCCTTATCCGGTAACTATCGTCTTGAGTCCAAC
{60R}
CCGGTAAGACACGACTTATCGCCACTGGCAGCAGCCACTG
{61R}
GTAACAGGATTAGCAGAGCGAGGTATGTAGGCGGTGCTAC
{62R}
AGAGTTCTTGAAGTGGTGGCCTAACTACGGCTACACTAGA
{63R}
AGAACAGTATTTGGTATCTGCGCTCTGCTGAAGCCAGTTA
{64R}
CCTTCGGAAAAAGAGTTGGTAGCTCTTGATCCGGCAAACA
{65R}
AACCACCGCTGGTAGCGGTGGTTTTTTTGTTTGCAAGCAG
{66R}
AACCACCGCTGGTAGCGGTGGTTTTTTTGTTTGCAAGCAG
{67R}
TGATCTTTTCTACGGGGTCTGACGCTCAGTGGAACGAAAA

{67F}
CGCGAGACGAAAGGGCCTCGTGATACGCCTATTTTTATAGGTAATGTCATGATAA

{29R}
TGCCACCTGACGTCTAAGAAACCATTATTATCATGACATTAACCTAT

{29F}
CCAAAATCCCTTAACGTGAGTTTTCGTTCCACTGAGCGTC
{30F}
AGACCCCGTAGAAAAGATCAAAGGATCTTCTTGAGATCCT
{31F}
TTTTTTCTGCGCGTAATCTGCTGCTTGCAAACAAAAAAAC
{32F}
CACCGCTACCAGCGGTGGTTTGTTTGCCGGATCAAGAGCT
{33F}
ACCAACTCTTTTTCGAAGGTAACTGGCTTCAGCAGAGCG
{34F}
CAGATACCAAATACTGTCCTTCTAGTGTAGCCGTAGTTAG
{35F}
GCCACCACTTCAAGAACTCTGTAGCACCGCCTACATACCT
{36F}
CGCTCTGCTAATCCTGTTACCAGTGGCTGCTGCCAGTGGC
{37F}
GATAAGTCGTGTTTACCGGGTTGGACTCAAGACGATAGT
{38F}
TACCGGATAAGGCGCAGCGGTCGGGCTGAACGGGGGGTTC
{39F}
GTGCACACAGCCCAGCTTGGAGCGAACGACCTACACCGAA
{40F}
CTGAGATACCTACAGCGTGAGCATTGAGAAAGCGCCACGC
{41F}
TTCCCGAAGGGAGAAAGGCGGACAGGTATCCGGTAAGCGG
{42F}
CAGGGTCGGAACAGGAGAGCGCACGAGGGAGCTTCCAGGG
{43F}
GGAAACGCCTGGTATCTTTATAGTCCTGTCGGGTTTCGCC
{44F}
ACCTCTGACTTGAGCGTCGATTTTTGTGAGCTCGTCAGG
{45F}
GGGGCGGAGCCTATGGAAAAACGCCAGCAACGCGGCCTTT
{46F}
TTAACGGTTCCTGGCCTTTTGCTGGCCTTTTGCTCACATGT
{47F}
TCTTTCCTGCGTTATCCCCTGATTCTGTGGATAACCGTAT
{48F}
TACCGCCTTTGAGTGAGCTGATACCGCTCGCCGCAGCCGA
{49F}
ACGACCGAGCGCAGCGAGTCAGTGACGAGGAAGCGGAAG
{50F}
AGCGCCCAATACGCAAACCGCCTCTCCCCGCGCGTTGGCC
{51F}
GATTCATTAATGCAGCTGGCACGACAGGTTTCCCGACTGG
{52F}
AAAGCGGGCAGTGAGCGCAACGCAATTAATGTGAGTTAGC
{53F}
TCACTCATTAGGCACCCCAGGCTTTACACTTTATGCTTCC
{54F}
GGCTCGTATGTTGTGTGGAATTGTGAGCGGATAACAATTT
{55F}
CACACAGGAAACAGCTATGACCATGATTACGAATTCGAGC
{56F}
TCGGTACCCGGGGATCCTCTAGAGTCGACCTGCAGGCATG
{57F}
CAAGCTTGGCACTGGCCGTCGTTTTACAACGTCGTGACTG

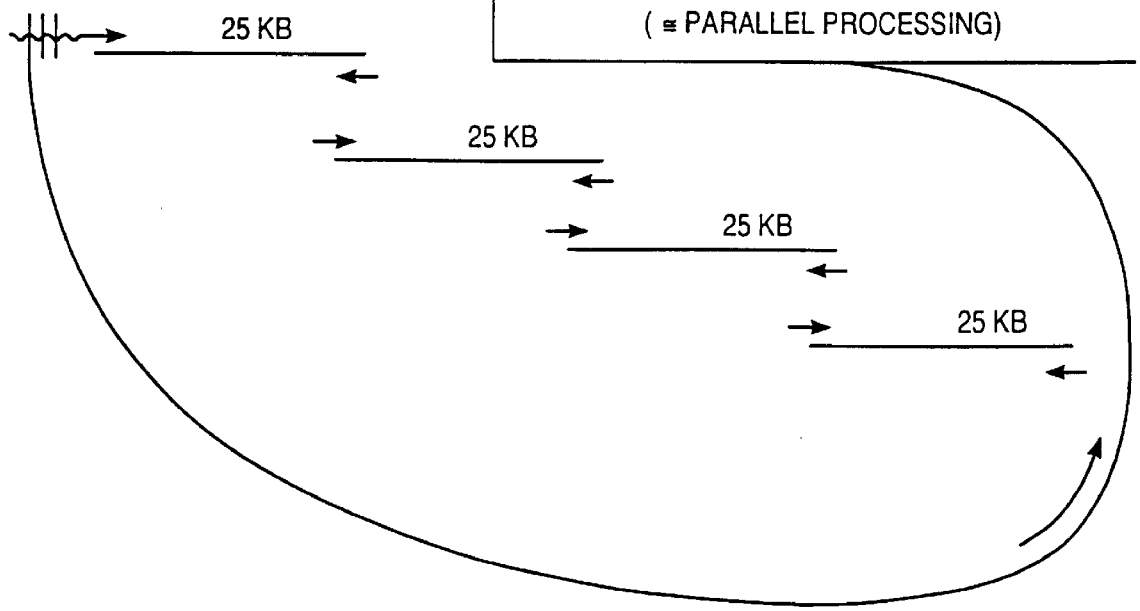
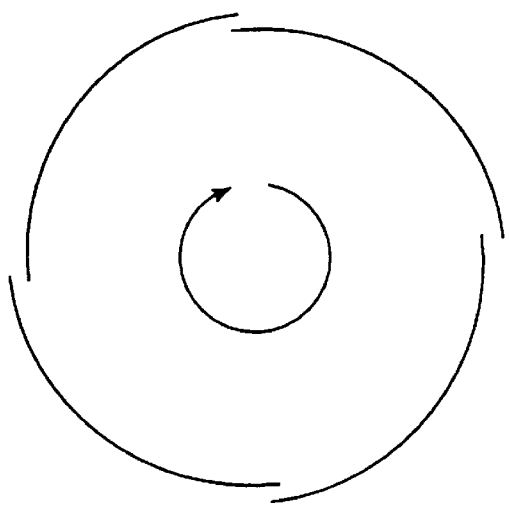
FIG. 8

# END-COMPLEMENTARY POLYMERASE REACTION

TECHNICAL FIELD

The present invention relates generally to the field of recombinant DNA technology and, more particularly, to improved methods for producing amplified heterogeneous populations of polynucleotides from limited quantities of DNA or RNA or other nucleic acids. The invention provides compositions and methods for a chain reaction amplification of a target polynucleotide species using a thermostable polymerase or other suitable polynucleotide polymerase compatible with the method.

BACKGROUND

Selective amplification of polynucleotides represents a major research goal of molecular biology, with particular importance in diagnostic and forensic applications, as well as for general manipulations of genetic materials and laboratory reagents.

The polymerase chain reaction (PCR) is a method by which a specific polynucleotide sequence can be amplified in vitro. PCR is an extremely powerful technique for amplifying specific polynucleotide sequences, including genomic DNA, single-stranded cDNA, and mRNA among others. As described in U.S. Pat. Nos. 4,683,202, 4,683,195, and 4,800,159 (which are incorporated herein by reference), PCR typically comprises treating separate complementary strands of a target nucleic acid with two oligonucleotide primers to form complementary primer extension products on both strands that act as templates for synthesizing copies of the desired nucleic acid sequences. By repeating the separation and synthesis steps in an automated system, essentially exponential duplication of the target sequences can be achieved.

A number of variations of the basic PCR methodology have been described. U.S. Pat. No. 5,066,584 discloses a method wherein single stranded DNA can be generated by the polymerase chain reaction using two oligonucleotide primers, one present in a limiting concentration. U.S. Pat. No. 5,340,728 discloses an improved method for performing a nested polymerase chain reaction (PCR) amplification of a targeted piece of DNA, wherein by controlling the annealing times and concentration of both the outer and the inner set of primers according to the method disclosed, highly specific and efficient amplification of a targeted piece of DNA can be achieved without depletion or removal of the outer primers from the reaction mixture vessel. U.S. Pat. No. 5,286,632 discloses recombination PCR (RPCR) wherein PCR is used with at least two primer species to add double-stranded homologous ends to DNA such that the homologous ends undergo in vivo recombination following transfection of host cells.

Horton et al. (1989) *Gene* 77: 61, discloses a method for making chimeric genes using PCR to generate overlapping homologous regions. In the Horton method, fragments of different genes that are to form the chimeric gene are generated in separate polymerase chain reactions. The primers used in these separate reactions are designed so that the ends of the different products of the separate reactions contain complementary sequences. When these separately produced PCR products are mixed, denatured and reannealed, the strands having matching sequences at their 3'-ends overlap and act as primers for each other. Extension of this overlap by DNA polymerase produces a molecule in which the original sequences are spliced together to form the chimeric gene.

Silver and Keerikatte (1989) *J. Virol.* 63: 1924 describe another variation of the standard PCR approach (which requires oligonucleotide primers complementary to both ends of the segment to be amplified) to allow amplification of DNA flanked on only one side by a region of known DNA sequence. This technique requires the presence of a known restriction site within the known DNA sequence and a similar site within the unknown flanking DNA sequence which is to be amplified. After restriction and recircularization, the recircularized fragment is restricted at an unique site between the two primers and the resulting linearized fragment is used as a template for PCR amplification.

Triglia et al. (1988) *Nucl.Acids Res.* 16: 8186, describe an approach which requires the inversion of the sequence of interest by circularization and re-opening at a site distinct from the one of interest, and is called "inverted PCR." A fragment is first created in which two unknown sequences flank on either side a region of known DNA sequence. The fragment is then circularized and cleaved with an unique restriction endonuclease which only cuts within the known DNA sequence creating a new fragment containing all of the DNA of the original fragment but which is then inverted with regions of known sequence flanking the region of unknown sequence. This fragment is then utilized as a PCR substrate to amplify the unknown sequence.

Vallette et al. (1989) *Nucl.Acids Res.* 17: 723 disclose using PCR in a specific approach which involves using a supercoiled plasmid DNA as a template for PCR and a primer bearing a mutated sequence which is incorporated into the amplified product. Using this method, DNA sequences may be inserted only at the 5'-end of the DNA molecule which one wishes to alter. Mole et al. (1989) *Nucl.Acids Res.* 17: 3319, used PCR to create deletions within existing expression plasmids. However, PCR was performed around the entire plasmid (containing the fragment to be deleted) from primers whose 5'-ends defined the region to be deleted. Self-ligation of the PCR product recircularized the plasmid.

U.S. Pat. No. 5,279,952 discloses a method for using PCR to generate mutations (e.g., deletions) and chimeric genes by forming head-to-tail concatemers of a known starting sequence and employing at least two PCR primers to amplify a DNA segment which is altered as compared to the known starting sequence.

Jones and Howard (1990) *BioTechnigues* 8: 178, report a site-specific mutagenesis method using PCR, termed recombinant circle PCR (RCPCR). In RCPCR, separate PCR amplifications (typically two) of a known polynucleotide generate products that, when combined, denatured, and annealed, form double-stranded DNA with discrete, cohesive single-stranded ends designed so that they may anneal and form circles of DNA.

Oliner et al. (1993) *Nucl. Acids. Res.* 21: 5192, report a method for engineering PCR products to contain terminal sequences identical to sequences at the two ends of a linearized vector such that co-transfection of the PCR product and linearized vector into a recombination-competent host cell results in formation of a covalently linked vector containing the PCR product, thus avoiding the need for in vitro ligation.

In spite of such recent advances, including PCR and its various modifications noted above, there exists a need for improved methods of identifying and cloning polynucleotides, for accurate in vitro amplification of selected polynucleotides, and for facile assembly of polynucleotides from a mixture of component oligonucleotides or polynucleotides without necessitating the use of DNA ligase. In particular, there is a need for a PCR amplification method which can be performed with (1) only a single primer species, or (2) with multiple overlapping polynucleotide fragments (or oligonucleotides) in the absence of a conventional PCR primer, and which can result in formation of an amplified product which can be a concatemer and/or which can be a covalently-closed circle. The present invention fulfills these and other needs.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference.

SUMMARY OF THE INVENTION

A basis of the present invention is the use of polymerase-mediated chain extension, such as for example PCR, in combination with at least two polynucleotides having complementary ends which can anneal whereby at least one of said polynucleotides has a free 3'-hydroxyl capable of polynucleotide chain elongation by a DNA polymerase, such as a thermostable polymerase (e.g., *Thermus aguaticus* (Taq) polymerase or *Thermococcus litoralis* (Vent™, New England Biolabs) polymerase or TthI polymerase (Perkin-Elmer). Although the method can be practiced using PCR, in some embodiments either a single primer species or no primer whatsoever is required, and hence PCR is not a necessary component of the general method.

In one embodiment, a target polynucleotide is contacted with a "bivalent primer" typically comprising an oligonucleotide having two regions of complementarity to the target polynucleotide: (1) a first portion which is in the 5' portion of the primer and which is substantially complementary to a sequence in the 5' portion of the sequence to be amplified (target sequence) in the target polynucleotide, and (2) a second portion which is in the 3' portion of the primer and which is substantially complementary to a sequence in the 3' portion of the sequence to be amplified (target sequence) in the target polynucleotide. The contacting is performed under conditions suitable for hybridization of the bivalent primer to the target polynucleotide, most often following thermal denaturation of the target polynucleotide if it is initially present as a double-stranded form. The target polynucleotide may be substantially homogeneous or may be present in a mixture of polynucleotide species (e.g., in a genome, biological sample, or mixture of synthetic polynucleotides). Subsequent or concomitant with the contacting of the bivalent primer to the target polynucleotide, a polynucleotide polymerase, such as a thermostable DNA polymerase, catalyzes, under suitable reaction conditions, polynucleotide synthesis (chain elongation) primed from the 3'-hydroxyl of the annealed bivalent primer to form a strand complementary to the target sequence, thereby forming a nascent complementary strand. Following completion of the nascent complementary strand spanning the target sequence, the target polynucleotide and the nascent strand are denatured, typically by elevation of temperature, and allowed to reanneal, typically by reduction of temperature, with another molecule of the bivalent primer species or with a complementary strand of a target polynucleotide or an amplified copy thereof. The denatured nascent strand species following the first elongation cycle will contain a copy of the target sequence and has a terminal repeat of its 5'-terminal sequence at the 3' terminus, resulting from the bivalent primer, and wherein the terminal repeat is of sufficient length to support annealing under PCR conditions to an overlapping complementary strand in a head-to-tail arrangement (see, FIG. 1). Following reannealing, the described polymerase elongation/denaturation/reannealing cycle is repeated from 1 to about 100 times as desired, resulting in formation of amplified product which comprises head-to-tail concatemers of the target sequence. The concatemers typically increase in length as the number of amplification cycles increase and as the amount of bivalent primer decreases. Following amplification forming concatameric head-to-tail repeats of the target sequence, the concatemer(s) can optionally be resolved, such as (1) by cleaving with a restriction endonuclease which cuts within (or at the termini of) the concatemeric unit(s), (2) by homologous recombination between concatemer units to form covalently closed circles, or (3) by cleavage with a restriction endonuclease followed by ligation with DNA ligase to form covalently closed circles and/or by direct transformation into host cells for in vivo ligation.

Often, a target polynucleotide sequence which is amplified as described above will form amplification intermediates in the form of cyclized DNA or spiral DNA (see, FIG. 2), as a result of the 3' terminus of an overlapped nascent strand annealing to the 3' terminus of an overlapped complementary strand forming a cyclized structure similar to a gapped circle; the cyclized structure has a strand with an extendable 3'-hydroxyl which can be extended with a DNA polymerase substantially lacking exonuclease activity (e.g., a thermostable polymerase such as Vent(exo⁻)™ or Klenow fragment, etc.) in a rolling circle format whereby the leading terminus of the nascent strand continually displaces the lagging portion of the nascent strand (see, FIG. 2) producing a concatemeric single strand emanating from the rolling circle intermediate. Most often, such rolling circle intermediates will form under dilute conditions more favorable to intramolecular cyclization of overlapped strands. Once a rolling circle intermediate is established, the template need not be denatured in order to continue amplification of the target sequence as in conventional PCR, thus avoiding the necessity of multiple thermal cycles of PCR to denature template (and the resultant time loss needed for heating and cooling). Often, however, the template is repeatedly denatured, annealed, and extended with polymerase in the presence of ribonucleotide or deoxyribonucleotides under suitable reaction conditions.

Furthermore, whether the method generates a rolling circle intermediate or linear concatemers, an advantage of the method is that it requires a substantially reduced amount of primer (bivalent primer) as compared to conventional PCR, since following the initial cycle(s) an increasing percentage of the priming of nascent strand synthesis is primed from 3'-hydroxyl groups of the amplified strands, rather than from the oligonucleotide primer(s). In the case of a rolling circle intermediate, theoretically only a single bivalent primer molecule is necessary to generate the rolling circle which then can produce multiple concatenated copies by rolling circle-style polymerase catalysis using a polymerase capable of strand displacement of the lagging edge of the nascent strand as replication proceeds around the cyclized template.

In an embodiment, a product polynucleotide is assembled from a plurality of component polynucleotides by formation of overlapped strands of alternating polarity and having substantially complementary termini (see, FIG. 3). This method employs a series of overlapping substantially complementary termini to determine the linear order of component sequences in the final product. Concomitant with or subsequent to formation of the overlapped strands of the component polynucleotides in a reaction, a polynucleotide polymerase (e.g., a thermostable DNA polymerase) under suitable reaction conditions catalyzes strand elongation from the 3'-hydroxyl portions of the overlapped (annealed) joints, filling in the portion between joints and processively displacing or processively degrading exonucleolytically the 5' termini of downstream component strands of the same polarity as the nascent strand elongates. After a cycle of chain elongation forming substantially double-stranded polynucleotides, the reaction conditions are altered (typically by increasing the temperature) to effect denaturation of the double-stranded polynucleotides, followed by altering the reaction conditions to permit reannealing of complementary strands or portions thereof (i.e., overlapping termini) to form molecules having overlapped termini (joints), and chain elongation by a polynucleotide polymerase under suitable reaction conditions catalyzes strand elongation from the 3'-hydroxyl portions of the overlapped (annealed) joints, as in the first cycle. One to about 100 cycles of denaturation/annealing/polymerization can be performed to generate a product comprising the component polynucleotide sequences covalently linked in linear order according to the order of the overlapping joints. In this embodiment, a product polynucleotide can be constructed from a plurality of smaller component polynucleotides (typically oligonucleotides) and enables assembly of a variety of products with alternate substitutable polynucleotide components at a given position serving as structural "alleles" (see, FIG. 4). The component polynucleotides are often provided in single-strand form, but may initially be present in double-strand form and be denatured (typically by elevated temperature) for the assembly of the product by PCR amplification. Substantially any type of product polynucleotide can be assembled in this way, including cloning and expression vectors, viral genomes, gene therapy vectors, genes (including chimeric genes), polynucleotides encoding peptide libraries, protein libraries, vector libraries, viral libraries, and the like. In a variation, one or more of the component polynucleotides represents a site-directed mutation or variable-sequence kernel. In a variation, PCR employing a low-fidelity polymerase is used to introduce additional sequence variation into the product polynucleotide(s) during amplification cycles. The method can be used to produce a library of sequence-variant product polynucleotides, if desired.

In an embodiment of the invention, very long distance PCR is provided, wherein PCR or other suitable amplification method is used to generate, in a single reaction or in parallel reactions which are subsequently pooled, a set of overlapping large DNA fragments which can be denatured and annealed to form very large (e.g., greater than 25 to 50 kilobases) DNA structures composed of overlapped single strands of DNA having alternating polarity with each overlapped joint providing an extendable 3'-hydroxyl group for forming phosphodiester bonds catalyzed by a polynucleotide polymerase in the presence of free ribonucleotide or deoxyribonucleotides. Typically, the method comprises forming at least three overlapping polynucleotides, wherein the 3' terminus of a first single-stranded polynucleotide is substantially complementary to the 3' terminus of a second single-stranded polynucleotide of the opposite polarity, and wherein the 5' terminus of said second single-stranded polynucleotide is substantially complementary to the 3' terminus of a third single-stranded polynucleotide having polarity identical to said first single-stranded polynucleotide, thereby generating an overlapped structure capable of chain elongation by a suitable polymerase to generate a double-stranded product spanning the three initial overlapped polynucleotides. With such a method, polynucleotides of 50 kb to 100 kb or more can be generated by a facile amplification method capable of generating amplification products much longer than is possible with conventional long-range PCR methods. The method can comprise parallel processing PCR reactions, wherein a plurality of primer sets are employed in a single reaction or multiple reactions which are subsequently pooled, each primer sets priming the PCR amplification of a polynucleotide sequence which comprises terminal sequences which are complementary to terminal sequences in at least one other amplification product produced by a different primer set, thus generating a set of overlapping PCR products with which a large product spanning the entire set of PCR products is generated by end-complementary polymerase reaction.

In some embodiments of the invention, the polynucleotides product(s) generated thereby are labelled, such as with radioisotopic, biotinyl, or fluorescent label moieties, by incorporation of labelled ribonucleotide or deoxyribonucleotides or the like into nascent polynucleotide by polymerase-mediated catalysis.

The invention also provides kits comprising a bivalent primer polynucleotide and/or a plurality of component polynucleotides and instructions for use describing the present end-complementary amplification method disclosed herein. Frequently, a polynucleotide polymerase, such as a thermostable DNA polymerase (Taq or Vent™ polymerase) is also present in the kit. Optionally, one or more target polynucleotides may be provided in the kit, such as for calibration and/or for use as a positive control to verify correct performance of the kit.

A further understanding of the nature and advantages of the invention will become apparent by reference to the remaining portions of the specification and drawings.

BRIEF DESCRIPTION OF THE DRAWINGS

FIG. 1A and 1B Schematic of bivalent primer and concatemer formation in end-complementary PCR.

FIG. 5A–E SEQ ID NOS. 3–136 shows oligonucleotides used to construct the 2.7 kb circular plasmid pl82SfiI by end-complementary polymerase reaction.

FIG. 8 Schematic for end-complementary polymerase reaction (ECPR) in conjunction with parallel-processing PCR to amplify very large polynucleotides, such as those larger than can be amplified reliably by conventional PCR using only a single primer set.

DESCRIPTION OF THE PREFERRED EMBODIMENTS

Figure 2:
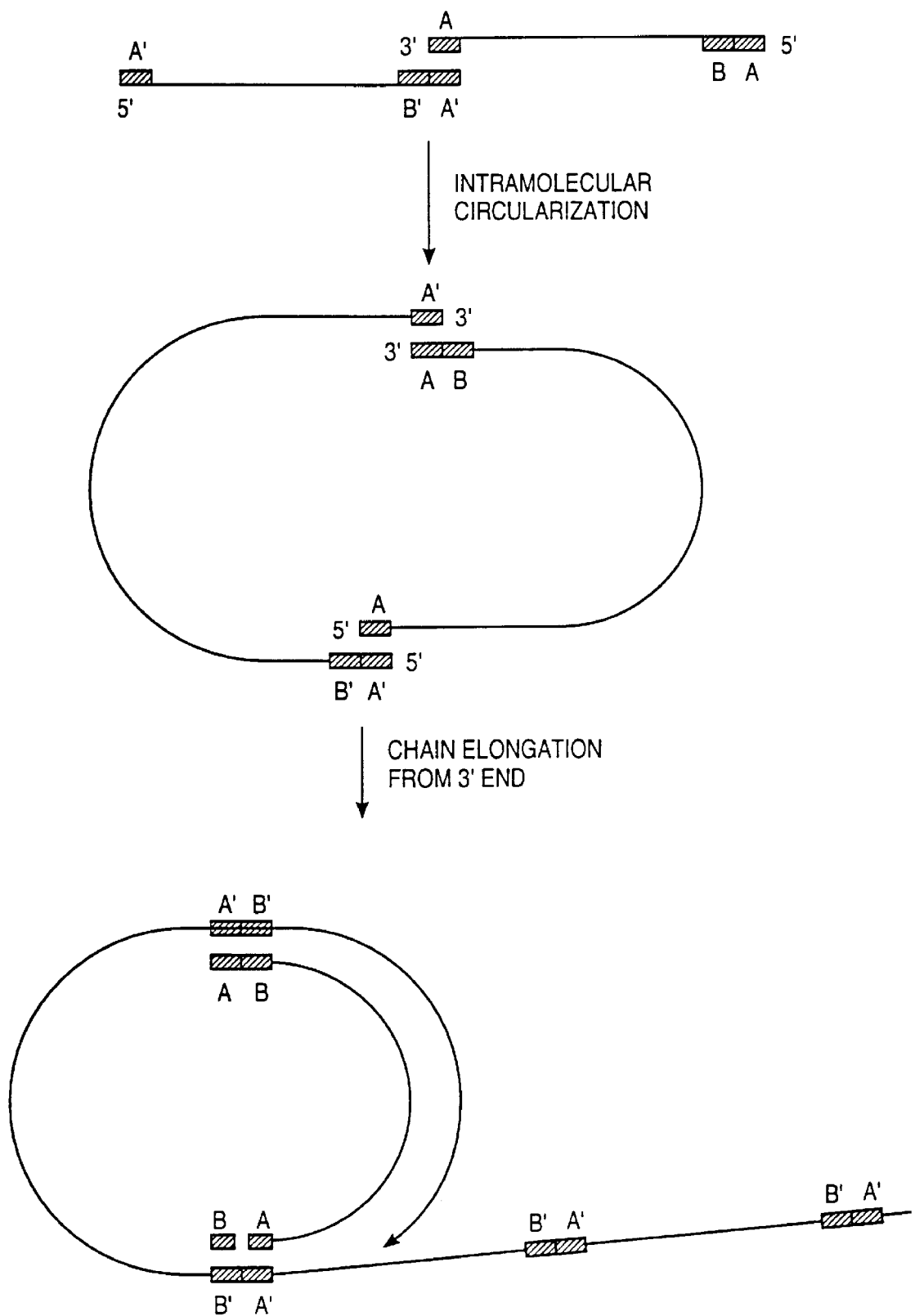
FIG. 2 Schematic depiction of cyclized intermediates and rolling circle amplification.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

Definitions

Unless specified otherwise, the conventional notation used herein portrays polynucleotides as follows: the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

As used herein, the term "polynucleotide" refers to a polymer composed of a multiplicity of nucleotide units (ribonucleotide or deoxyribonucleotide or related structural variants) linked via phosphodiester bonds. A polynucleotide can be of substantially any length, typically from about 10 nucleotides to about $1 \times 10^9$ nucleotides or larger. As used herein, an "oligonucleotide" is defined as a polynucleotide of from 6 to 100 nucleotides in length. Thus, an oligonucleotide is a subset of polynucleotides.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "corresponds to" is used herein to mean that a polynucleotide sequence is homologous (i.e., is identical, not strictly evolutionarily related) to all or a portion of a reference polynucleotide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 12 nucleotides in length, frequently at least 15 to 18 nucleotides in length, and often at least 25 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"comparison window", as used herein, refers to a conceptual segment of at least 12 contiguous nucleotide positions wherein a polynucleotide sequence may be compared to a reference sequence of at least 12 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

The primers herein are selected to be substantially complementary to the different strands of each specific sequence to be amplified. The primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

As used herein, a "bivalent primer" is a polynucleotide having two regions of complementarity to a predetermined target polynucleotide: (1) a first portion which is in the 5' portion of the bivalent primer and which is substantially complementary to a sequence in the 5' portion of the sequence to be amplified (target sequence) in the target polynucleotide, and (2) a second portion which is in the 3' portion of the primer and which is substantially complementary to a sequence in the 5' portion of the sequence to be amplified (target sequence) in the target polynucleotide. The portion of the bivalent primer which is substantially complementary to a sequence in the 5' portion of the sequence to be amplified (target sequence) is sufficiently long and sufficiently complementary to the target sequence to anneal under the reaction conditions and serve as an extendable primer for the polymerase to catalyze chain elongation. Similarly, the portion of the bivalent primer which is substantially complementary to a sequence in the 5' portion of the sequence to be amplified (target sequence) is sufficiently long and sufficiently complementary to the target sequence to anneal under the reaction conditions and serve as an extendable primer for the polymerase to catalyze chain elongation. Practitioners in the art will select at their discretion the specific structure of the bivalent primer(s) to be used in view of the necessity for annealing to the target. Typically, the portions of the bivalent primer which is substantially complementary to a sequence in the 5' and 3' portions of the sequence to be amplified (target sequence) are each at least 12 to 15 nucleotides in length, often 18 to 20 nucleotides in length, and are preferably 100 percent identical to the complement of the annealing portion of the target sequence. Often, bivalent primers of the invention are oligonucleotides.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single-stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15–25 or more nucleotides, although it may contain fewer nucleotides. Short primer molecules generally require cooler temperatures to form sufficiently stable hybrid complexes with template. In some embodiments, the primers can be large polynucleotides, such as from about 200 nucleotides to several kilobases or more.

As used herein, "suitable reaction conditions" are those conditions suitable for conducting PCR amplification using conventional reagents. Such conditions are known or readily established by those of skill in the art, and can be exemplified by the reaction conditions used in U.S. Pats. 4,683,202, 4,683,195, and 4,800,159, which are incorporated herein by reference. As one example and not to limit the invention, suitable reaction conditions can comprise: 0.2mM each dNTP, 2.2 mM $MgCl_2$, 50 mM KCl, 10 mM Tris-HCl pH 9.0, 0.1% Triton X-100.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for PCR and many polynucleotide enzymatic reactions and manipulations are generally physiological conditions. In general, in vitro physiological conditions comprise 50–200 mM NaCl or KCl, pH 6.5–8.5, 20°–45° C. and 0.001–10 mM divalent cation (e.g., $Mg^{++}Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with option of divalent cation(s) and/or metal chelators and/or nonionic detergents and/or membrane fractions and/or antifoam agents and/or scintillants.

As used herein, the terms "label" or "labeled" refers to incorporation of a detectable marker, e.g., by incorporation of a radiolabelled nucleotide or incorporation of nucleotide having biotinyl moieties that can be detected by marked avidin (e.g., streptavidin containing a fluorescent marker or enzymatic activity that can be detected by optical or colorimetric methods). Various methods of labeling polynucleotides are known in the art and may be used. Examples of labels include, but are not limited to, the following: radio-isotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, and the like. In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "recombinant" used herein refers to macromolecules produced by recombinant DNA techniques wherein the gene coding for a polypeptide is cloned by known recombinant DNA technology. For example, an amplified or assembled product polynucleotide may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host. Alternatively, the product polynucleotide may serve a non-coding function (e.g., promoter, origin of replication, ribosome-binding site, etc.).

Generally, the nomenclature used hereafter and many of the laboratory procedures in cell culture, molecular genetics, and nucleic acid chemistry and hybridization described below are those well known and commonly employed in the art. Standard techniques are used for recombinant nucleic acid methods, polynucleotide synthesis, in vitro polypeptide synthesis, and the like and microbial culture and transformation (e.g., electroporation). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.; each of which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Stockton Press, New York, N.Y. (1989); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; and U.S. Pat. Nos. 4,683,202 and 4,965,188, each of which are incorporated herein by reference) and exemplified hereinbelow.

Overview

A basis of the present invention is the use of polymerase in combination with at least two polynucleotides having complementary ends which can anneal whereby at least one of said polynucleotides has a free 3'-hydroxyl capable of polynucleotide chain elongation by a DNA polymerase, such as a thermostable polymerase (e.g., *Thermus aguaticus* (Taq) polymerase or *Thermococcus litoralis* (Vent™) polymerase. In an embodiment, the method is performed using PCR, typically with multiple cycles of heat denaturation and DNA synthesis. However, there are several variations of the basic method of end-complementary polymerase reaction which are exemplified hereinbelow and which shall be evident to the skilled artisan in view of the present specification. Some variations do not require primers and/or sequential cycles of thermal denaturation.

In embodiments where the product size increases with he number of denaturation, annealing, and extension cycles (e.g., as the mean length of concatemers increase), it is typically advantageous to increase the denaturation temperature, and optionally increase the reannealing time, for subsequent cycles. Such conditions are readily optimized by the practitioner using pilot reactions to establish a calibration curve for any particular embodiment.

Single-Primer Amplification

A target polynucleotide is contacted with a bivalent primer typically comprising an oligonucleotide having two regions of complementarity to the target polynucleotide: (1) a first portion which is in the 5' portion of the primer and which is substantially complementary to a sequence in the 5' portion of the sequence to be amplified (target sequence) in the target polynucleotide, and (2) a second portion which is in the 3' portion of the primer and which is substantially complementary to a sequence in the 3' portion of the sequence to be amplified (target sequence) in the target polynucleotide. The contacting is performed under conditions suitable for hybridization of the bivalent primer to the target polynucleotide for polymerase-mediated chain elongation, most often following thermal denaturation of the target polynucleotide if it is initially present as a double-stranded form.

The first portion of the bivalent primer which is in the 5' portion of the primer and which is substantially complementary to a sequence in the 3' portion of the sequence to be amplified (target sequence) in the target polynucleotide is typically at least 12 nucleotides in length, often at least 15 nucleotides in length, frequently at least 18 nucleotides in length, and is commonly 20 to 25 or more nucleotides in length, but usually does not exceed 10,000 nucleotides in length and is frequently less than 50 to 500 nucleotides in length. The first portion of the bivalent primer is substantially identical to the complement of a sequence at the 3' end of the target sequence, however there may be additional terminal nucleotides of the first portion of the bivalent primer which are substantially non-identical to a target sequence or its complement. Such terminal nucleotides must be substantially non-interfering so that their presence does not significantly inhibit the capability of the bivalent primer to selectively anneal to the target sequence and initiate chain elongation under suitable reaction conditions in the presence of polymerase. Although the first portion of the bivalent primer is substantially identical to the complement of a sequence at the 5' end of the target sequence, it need not be exactly identical; often a sequence identity of at least 80 percent is sufficient, typically at least 90 percent sequence identity is present, and preferably at least 95 percent or 100 percent sequence identity is present. As the length of the complementary sequence increases, typically the percentage of sequence identity necessary for specific annealing decreases within certain limits (pp. 399–407, in Berger and Kimmel, *Methods in Enzymology. Volume* 152, *Guide to Molecular Cloning Techniques* (1987), Academic Press, Inc., San Diego, Calif., which is incorporated herein by reference).

The second portion of the bivalent primer which is in the 3' portion of the primer and which is substantially complementary to a sequence in the 3' portion of the sequence to be amplified (target sequence) in the target polynucleotide is typically at least 12 nucleotides in length, often at least 15 nucleotides in length, frequently at least 18 nucleotides in length, and is commonly 20 to 25 or more nucleotides in length, but usually does not exceed 10,000 nucleotides in length and is frequently less than 50 to 500 nucleotides in length. The second portion of the bivalent primer is substantially identical to the complement of a sequence at the 5' end of the target sequence, however there may be additional terminal nucleotides of the second portion of the bivalent primer which are substantially non-identical to a target sequence or its complement. Such terminal nucleotides must be substantially non-interfering so that their presence does not significantly inhibit the capability of the bivalent primer to selectively anneal to the target sequence and initiate chain elongation under suitable reaction conditions in the presence of polymerase. Although the second portion of the bivalent primer is substantially identical to the complement of a sequence at the 3' end of the target sequence, it need not be exactly identical; often a sequence identity of at least 80 percent is sufficient, typically at least 90 percent sequence identity is present, and preferably at least 95 percent or 100 percent sequence identity is present. In some embodiments, sequence identity of less than 80 percent is practicable, but the amount of sequence identity and length of overlap for the joints is determined by the discretion of the practitioner.

The amount of sequence identity necessary for any given application will vary depending on several factors including: (1) complexity of the population of polynucleotides in which the target polynucleotide(s) is/are present, (2) temperature and ionic strength, (3) sequence composition of the target sequence, (4) length of sequence identity, and (5) size of the primer. Practitioners will select bivalent primers having a first portion with sufficient sequence identity and length to serve as selective amplification primers which specifically hybridize to the desired target polynucleotide(s). Specific hybridization is the formation of hybrids between a primer polynucleotide and a target polynucleotide, wherein the primer polynucleotide preferentially hybridizes to the target DNA such that, for example, at least one discrete band can be identified on a gel of amplification products obtained from amplification of genomic DNA prepared from eukaryotic cells that contain (or are spiked with) the target polynucleotide sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate primer sequences and hybridization conditions (see, Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987), Academic Press, Inc., San Diego, Calif.; PCR *Protocols: A Guide to Methods and Applications*, eds. Innis, Gelfland, Snisky, and White, Academic Press, San Diego, Calif. (1990); Benton WD and Davis RW (1977) *Science* 196: 180; Goodspeed et al. (1989) *Gene* 76: 1; Dunn et al. (1989) *J. Biol. Chem.* 264: 13057 which are incorporated herein by reference.

The target polynucleotide may be substantially homogeneous or may be present in a mixture of polynucleotide species (e.g., in a genome, biological sample, or mixture of synthetic polynucleotides). Subsequent or concomitant with the contacting of the bivalent primer to the target polynucleotide, a polynucleotide polymerase, such as a thermostable DNA polymerase, e.g., Taq polymerase, TThI polymerase (Perkin Elmer) or Vent™ (New England Biolabs, Beverly, Mass.), catalyzes, under suitable reaction conditions, polynucleotide synthesis (chain elongation) primed from the 3'-hydroxyl of the annealed bivalent primer to form a strand complementary to the target sequence, thereby forming a nascent complementary strand. Following completion of the nascent complementary strand spanning the target sequence, the target polynucleotide and the nascent strand are denatured, typically by elevation of temperature, and allowed to reanneal, typically by reduction of temperature, with another molecule of the bivalent primer species or with a complementary strand of a target polynucleotide or an amplified copy thereof. The denatured nascent strand species following the first elongation cycle will contain a copy of the target sequence and has a terminal repeat of its 5'-terminal sequence at the 3' terminus, resulting from the bivalent primer, and wherein the terminal repeat is of sufficient length to support annealing under PCR conditions to an overlapping complementary strand in a head-to-tail arrangement (see, FIG. 1). Following reannealing, the described polymerase elongation/denaturation/reannealing cycle is repeated from 1 to about 100 times as desired, resulting in formation of amplified product which comprises head-to-tail concatemers of the target sequence. The concatemers typically increase in length as the number of amplification cycles increase and as the amount of bivalent primer decreases. Following amplification forming concatameric head-to-tail repeats of the target sequence, the concatemer(s) can optionally be resolved, such as (1) by cleaving with a restriction endonuclease which cuts within (or at the termini of) the concatemeric unit(s), (2) by homologous recombination between concatemer units to form covalently closed circles, or (3) by cleavage with a restriction endonuclease followed by ligation with DNA ligase to form covalently closed circles and/or by direct transformation into host cells for in vivo ligation.

By this method, a single primer (bivalent primer) is used to amplify a target polynucleotide sequence having a predetermined 5' terminal sequence and a predetermined 3' terminal sequence. The predetermined 5' terminal sequence and a predetermined 3' terminal sequence may be contained internally within a larger polynucleotide; hence the use of the term "terminal" refers only to their terminality within the target sequence, not necessarily the complete target polynucleotide which may be a superset of the target sequence.

Rolling Circle PCR Amplification

Often, a target polynucleotide sequence which is amplified by the present method will form amplification intermediates in the form of cyclized DNA (see, FIG. 2), as a result of the 3' terminus of an overlapped nascent strand annealing to the 3' terminus of an overlapped complementary strand forming a cyclized (circular) structure similar to a gapped circle. The cyclized structure has a strand with an extendable 3'-hydroxyl which can be extended with a DNA polymerase substantially lacking exonuclease activity (e.g., a thermostable polymerase such as Vent(exo⁻)™ or Klenow fragment, etc.) in a rolling circle format whereby the leading terminus of the nascent strand continually displaces the lagging portion of the nascent strand (see, FIG. 2) producing concatemeric single strand propagating from the rolling circle intermediate. Most often, such rolling circle intermediates will form under dilute conditions more favorable to intramolecular cyclization of overlapped strands than to formation of additional intermolecular overlaps. Once a rolling circle intermediate is established, the template need not be denatured in order to continue amplification of the target sequence as in conventional PCR, since the polymerase continues around the circle processively. Thus, the advantageous formation of the rolling circle intermediate in the present method avoids the necessity of multiple thermal cycles of PCR to repeatedly denature and renature the amplification template (and the resultant time loss needed for heating and cooling).

Overlapped Assembly of Polynucleotides

The present invention also provides for assembly of one or more product polynucleotide(s) from a plurality of component polynucleotides which have overlapping complementary sequence portions at their termini. The component polynucleotides are conveniently single-stranded oligonucleotides, but can include double-stranded polynucleotides (which are generally denatured with elevated temperature) and long single-stranded polynucleotides.

Figure 3:
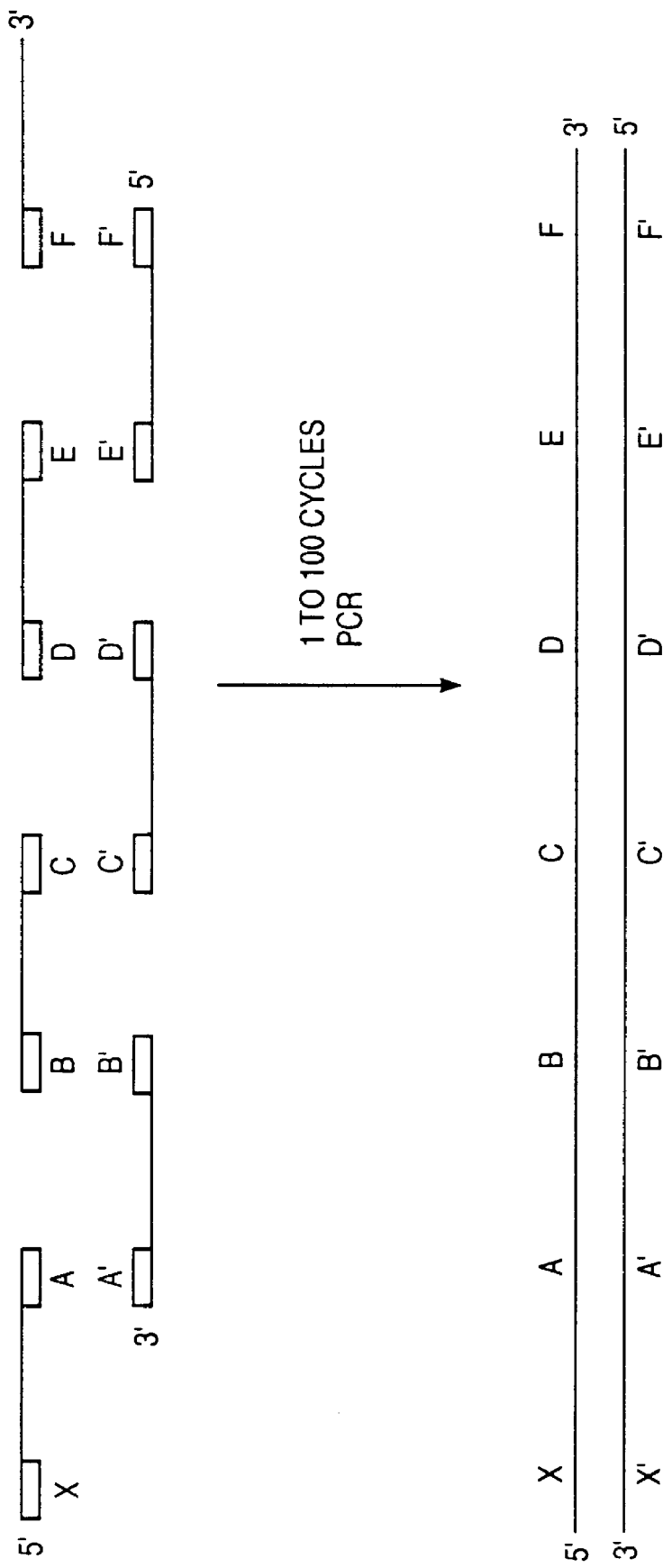
FIG. 3 Schematic of overlapping fragment PCR for construction and amplification of larger products from component polynucleotides.
Figure 4:
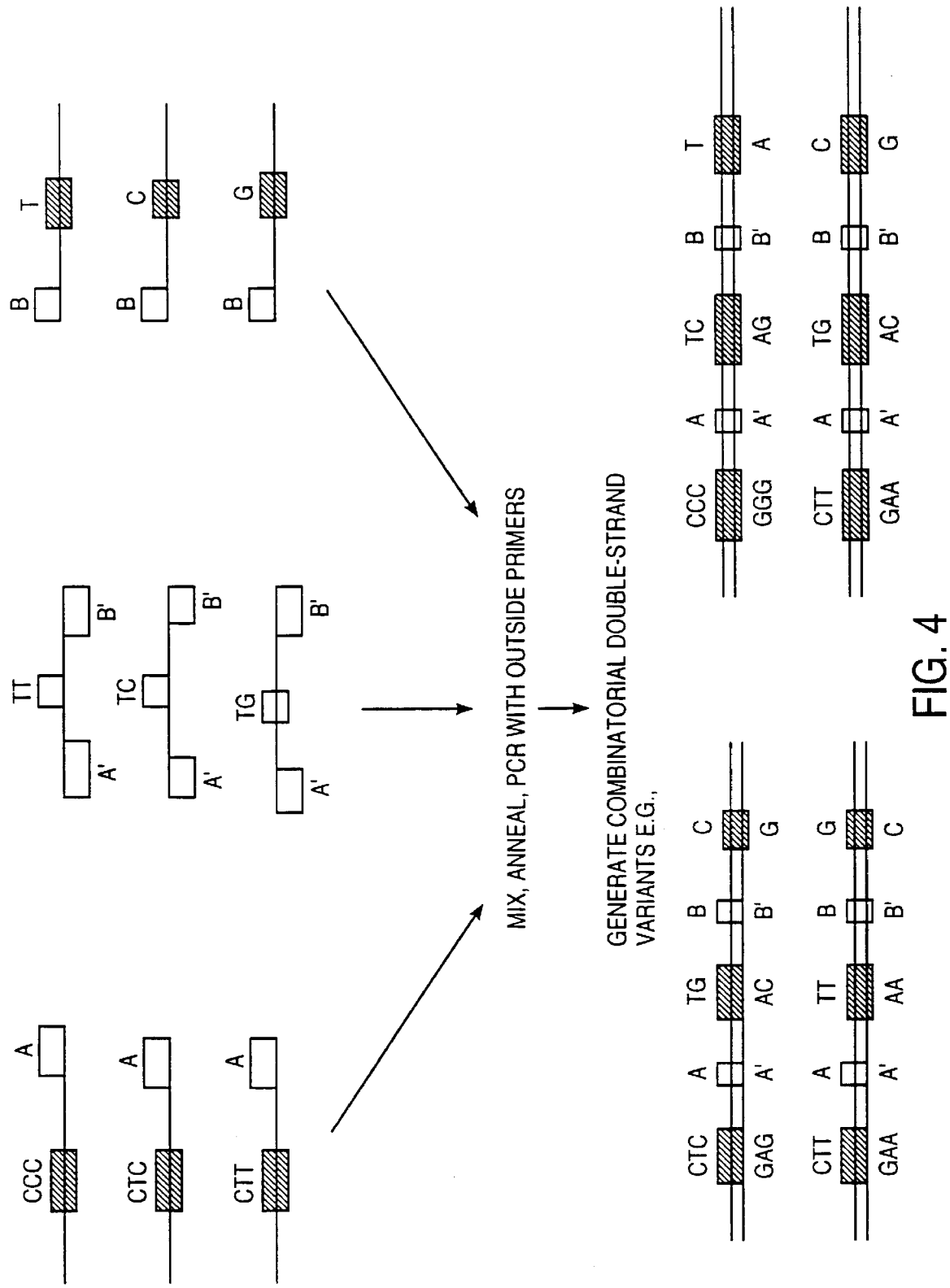
FIG. 4 Schematic of multiple "alleles" with overlapping fragment PCR.

A desired product polynucleotide (or polynucleotide library) is assembled from a plurality of component polynucleotides by formation of overlapped strands of alternating polarity and having substantially complementary termini (see, FIG. 3). This method employs a series of overlapping substantially complementary termini to determine the linear order of component sequences in the final product. Concomitant with or subsequent to formation of the overlapped strands of the component polynucleotides in a reaction, a polynucleotide polymerase (e.g., a thermostable DNA polymerase) under suitable reaction conditions catalyzes strand elongation from the 3'-hydroxyl portions of the overlapped (annealed) joints, filling in the portion between joints and processively displacing or processively degrading exonucleolytically the 5' termini of downstream component strands of the same polarity as the nascent strand elongates. After a cycle of chain elongation forming substantially double-stranded polynucleotides, the reaction conditions are altered (typically by increasing the temperature) to effect denaturation of the double-stranded polynucleotides, followed by altering the reaction conditions to permit reannealing of complementary strands or portions thereof (i.e., overlapping termini) to form molecules having overlapped termini (joints), and chain elongation by a polynucleotide polymerase under suitable reaction conditions catalyzes strand elongation from the 3'-hydroxyl portions of the overlapped (annealed) joints, as in the first cycle. One to about 100 cycles of denaturation/annealing/polymerization can be performed to generate a product comprising the component polynucleotide sequences covalently linked in linear order according to the order of the overlapping joints. In this embodiment, a product polynucleotide can be constructed from a plurality of smaller component polynucleotides (typically oligonucleotides) and enables assembly of a variety of products with alternate substitutable polynucleotide components at a given position serving as structural "alleles" (see, FIG. 4). The component polynucleotides are often provided in single-strand form, but may initially be present in double-strand form and be denatured (typically by elevated temperature) for the assembly of the product by PCR amplification. Substantially any type of product polynucleotide can be assembled in this way, including cloning and expression vectors, viral genomes, gene therapy vectors, genes (including chimeric genes), polynucleotides encoding peptide libraries, and the like. In a variation, one or more of the component polynucleotides represents a site-directed mutation or variable-sequence kernal. In a variation, PCR employing a low-fidelity polymerase is used to introduce additional sequence variation into the product polynucleotide(s) during amplification cycles. The method can be used to produce a library of sequence-variant product polynucleotides, if desired.

Kits

The invention also provides kits comprising a bivalent primer polynucleotide and/or a plurality of component polynucleotides and instructions for use describing the present end-complementary amplification method disclosed herein. Frequently, a polynucleotide polymerase, such as a thermostable DNA polymerase (Taq or Vent™ polymerase) is also present in the kit. Optionally, one or more target polynucleotides may be provided in the kit, such as for calibration and/or for use as a positive control to verify correct performance of the kit.

General Aspects

The target polynucleotides or component polynucleotides may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al., Molecular Cloning: A Laboratory Manual, (New York: Cold Spring Harbor Laboratory, 1982), pp. 280–281. Alternatively, the polynucleotides may be produced by chemical synthesis by any of the art-recognized methods.

Any specific nucleic acid sequence can be produced by the present process. It is only necessary that a sufficient number of bases at both ends of the sequence be known in sufficient detail so that a bivalent primers can be prepared which will hybridize to the desired sequence and at relative positions along the sequence such that an extension product initially synthesized from the bivalent primer, when it is separated from its template (complement), can anneal with a stand of the opposite polarity to form an overlapped joint of a head-to-tail concatemer and serve as a template for extension of the 3'-hydroxyl from each overlapped joint. The greater the knowledge about the bases at both ends of the sequence, the greater can be the specificity of the primer for the target nucleic acid sequence, and thus the greater the efficiency of the process. It will be understood that the word bivalent primer as used hereinafter may refer to more than one bivalent primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand.

The polynucleotide primers may be prepared using any suitable method, such as, for example, the phosphotriester and phosphodiester methods, or automated embodiments thereof. In one such automated embodiment diethylphosphoramidites are used as starting materials and may be synthesized as described by Beaucage et al. (1981) *Tetrahedron Letters* 22: 1859. One method for synthesizing oligonucleotides on a modified solid support is described in U.S. Pat. No. 4,458,066. It is also possible to use a primer which has been isolated from a biological source (such as a restriction endonuclease digest or the like).

The specific nucleic acid sequence is produced by using the target polynucleotide containing that sequence as a template. If the target polynucleotide contains two strands, it is necessary to separate the strands of the nucleic acid before it can be used as the template, either as a separate step or simultaneously with the synthesis of the primer extension products. This strand separation can be accomplished by any suitable denaturing method including physical, chemical or enzymatic means. One physical method of separating the strands of the polynucleotide involves heating the polynucleotide until it is substantially denatured. Typical heat denaturation may involve temperatures ranging from about 80° to 105° C. for times ranging from about 10 seconds to about 10 minutes or more. Strand separation may also be induced by an enzyme from the class of enzymes known as helicases or the enzyme RecA, which has helicase activity and in the presence of rATP is known to denature DNA. The reaction conditions suitable for separating the strands of polynucleotides with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67, and techniques for using RecA are reviewed in C. Radding, Ann. Rev. Genetics, 16:405–37 (1982).

PCR synthesis can be performed using any suitable method. Generally it occurs in a buffered aqueous solution, preferably at a pH of 7–9, most preferably about 8. The bivalent primer(s) is/are added in suitable amounts (molar ratio to target), typically less than conventional PCR methods because of the self-priming nature of the overlapped concatemers. The deoxyribonucleoside triphosphates dATP, dCTP, dGTP and TTP are also added to the synthesis mixture in adequate amounts and the resulting solution is heated to about 85°–100° C. for from about 1 to 10 minutes, preferably from 1 to 4 minutes. After this heating period the solution is allowed to cool to from 20°–40° C., which is preferable for the primer hybridization. To the cooled mixture is added an agent for polymerization, and the reaction is allowed to occur under conditions known in the art. This synthesis reaction may occur at from room temperature up to a temperature above which the agent for polymerization no longer functions efficiently. Thus, for example, if DNA polymerase is used as the agent for polymerization, the temperature is generally no greater than about 45° C. The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of the primer and proceed in the 5' direction along the template strand, until synthesis terminates, producing molecules of different lengths.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

The steps of strand separation and extension product synthesis can be repeated as often as needed to produce the desired quantity of the specific nucleic acid sequence. The amount of the specific nucleic acid sequence produced will accumulate in an exponential fashion and the average size of the product will also increase as the length of the concatemers increases with each cycle.

The method herein may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells.

EXPERIMENTAL EXAMPLES

The following examples are offered by way of example and not by way of limitation. Variations and alternate embodiments will be apparent to those of skill in the art.

Example 1.

LacZ alpha gene reassembly

This example shows that small fragments having overlapping regions of homology can be amplified and reassembled by PCR amplification methods in the absence of any primer.

1) Substrate preparation

The substrate for the reassembly reaction was the dsDNA polymerase chain reaction ("PCR") product of the wild-type LacZ alpha gene from pUC18. (Gene Bank No. X02514) The primer sequences were 5' AAAGCGTCGATTTTTGT-GAT3' (SEQ ID NO:1) and 5' ATGGGGTTCCGCGCA-CATTT3' (SEQ ID NO:2). The free primers were removed from the PCR product by Wizard PCR prep (Promega, Madison Wis.) according to the manufacturer's directions. The removal of the free primers was found to be important.

2) DNAseI digestion

About 5 $\mu$g of the DNA substrate was digested with 0.15 units of DNAseI (Sigma, St. Louis Mo.) in 100 $\mu$l of (50 mM Tris-HCl pH 7.4, 1 mM $MgCl_2$), for 10–20 minutes at room temperature. The digested DNA was run on a 2% low melting point agarose gel. Fragments of 10–70 basepairs (bp) were purified from the 2% low melting point agarose gels by electrophoresis onto DE81 ion exchange paper (Whatman, Hillsborough Oreg.). The DNA fragments were eluted from the paper with 1 M NaCl and ethanol precipitated.

3) DNA Reassembly

The purified fragments were resuspended at a concentration of 10–30 ng/$\mu$l in PCR Mix (0.2 mM each dNTP, 2.2 mM $MgCl_2$, 50 mM KCl, 10 mM Tris-HCl pH 9.0, 0.1% Triton X- 20 100, 0.3 $\mu$l Taq DNA polymerase, 50 $\mu$l total volume). No primers were added at this point. A reassembly program of 94° C. for 60 seconds, 30–45 cycles of [94° C. for 30 seconds, 50°–55° C. for 30 seconds, 72° C. for 30 seconds] and 5 minutes at 72° C. was used in an MJ Research (Watertown Mass.) PTC-150 thermocycler. The PCR reassembly of small fragments into larger sequences was followed by taking samples of the reaction after 25, 30, 35, 40, and 45 cycles of reassembly.

Whereas the reassembly of 100–200 bp fragments can yield a single PCR product of the correct size, 10–50 base fragments typically yield some product of the correct size, as well as products of heterogeneous molecular weights. Most of this size heterogeneity appears to be due to single-stranded sequences at the ends of the products, since after restriction enzyme digestion a single band of the correct size is obtained.

4) PCR with primers

After dilution of the reassembly product into the PCR Mix with 0.8 $\mu$M of each of the above primers (SEQ ID Nos: 1 and 2) and about 15 cycles of PCR, each cycle consisting of (94° C. for 30 seconds, 50° C. for 30 seconds and 72° C. for 30 seconds), a single product of the correct size was obtained.

5) Cloning and analysis

The PCR product from step 4 above was digested with the terminal restriction enzymes BamHI and EcoO109 and gel purified as described above in step 2. The reassembled fragments were ligated into pUC18 digested with BamHI and EcoO109. E. coli were transformed with the ligation mixture under standard conditions as recommended by the manufacturer (Stratagene, San Diego Calif.) and plated on agar plates having 100 $\mu$g/ml ampicillin, 0.004% X-gal and 2mM IPTG. The resulting colonies having the HinDIII-NheI fragment which is diagnostic for the ++ recombinant were identified because they appeared blue.

This Example illustrates that a 1.0 kb sequence carrying the LacZ alpha gene can be digested into 10–70 bp fragments, and that these gel purified 10–70 bp fragments can be reassembled to a single product of the correct size, such that 84% (N=377) of the resulting colonies are LacZ$^+$ (versus 94% without shuffling). This principal finding is extended substantially in the present invention to assemble component polynucleotides into product polynucleotides, and the component polynucleotides are not limited to randomly digested fragments of a naturally-occurring gene sequence.

The DNA encoding the LacZ gene from the resulting LacZ$^-$ colonies was sequenced with a sequencing kit (United States Biochemical Co., Cleveland Ohio) according to the manufacturer's instructions and the genes were found to have point mutations due to the reassembly process (Table 1). 11/12 types of substitutions were found, and no frameshifts.

TABLE 1

Mutations introduced by mutagenic shuffling

| Transitions | Frequency | Transversions | Frequency |
|---|---|---|---|
| G-A | 6 | A-T | 1 |
| A-G | 4 | A-C | 2 |
| C-T | 7 | C-A | 1 |
| T-C | 3 | C-G | 0 |
|  |  | G-C | 3 |
|  |  | G-T | 2 |
|  |  | T-A | 1 |
|  |  | T-G | 2 |

A total of 4,437 bases of shuffled lacZ DNA were sequenced.

The rate of point mutagenesis during DNA reassembly from 10–70 bp pieces was determined from DNA sequencing to be 0.7 % (N=4,473), which is similar to error-prone PCR. Without being limited to any theory it is believed that the rate of point mutagenesis may be lower if larger fragments are used for the reassembly, or if a proofreading polymerase is added.

When plasmid DNA from 14 of these point-mutated LacZ$^-$ colonies were combined and again reassembled/shuffled by the method described above, 34% (N=291) of the resulting colonies were LacZ$^+$, and these colonies presumably arose by recombination of the DNA from different colonies.

The expected rate of reversal of a single point mutation by error-prone PCR, assuming a mutagenesis rate of 0.7% (10), would be expected to be <1%.

Thus large DNA sequences can be reassembled from a random mixture of small fragments by a reaction that is surprisingly efficient and simple. One application of this technique is the recombination or shuffling of related sequences based on homology. A second application is the assembly of a large product polynucleotide by PCR amplification of component polynucleotides (oligonucleotides) having overlapping regions of homology to form annealed joints during PCR amplification.

Example 2
One-Step Circular Plasmid Assembly From Oligonucleotides

Figure 6:
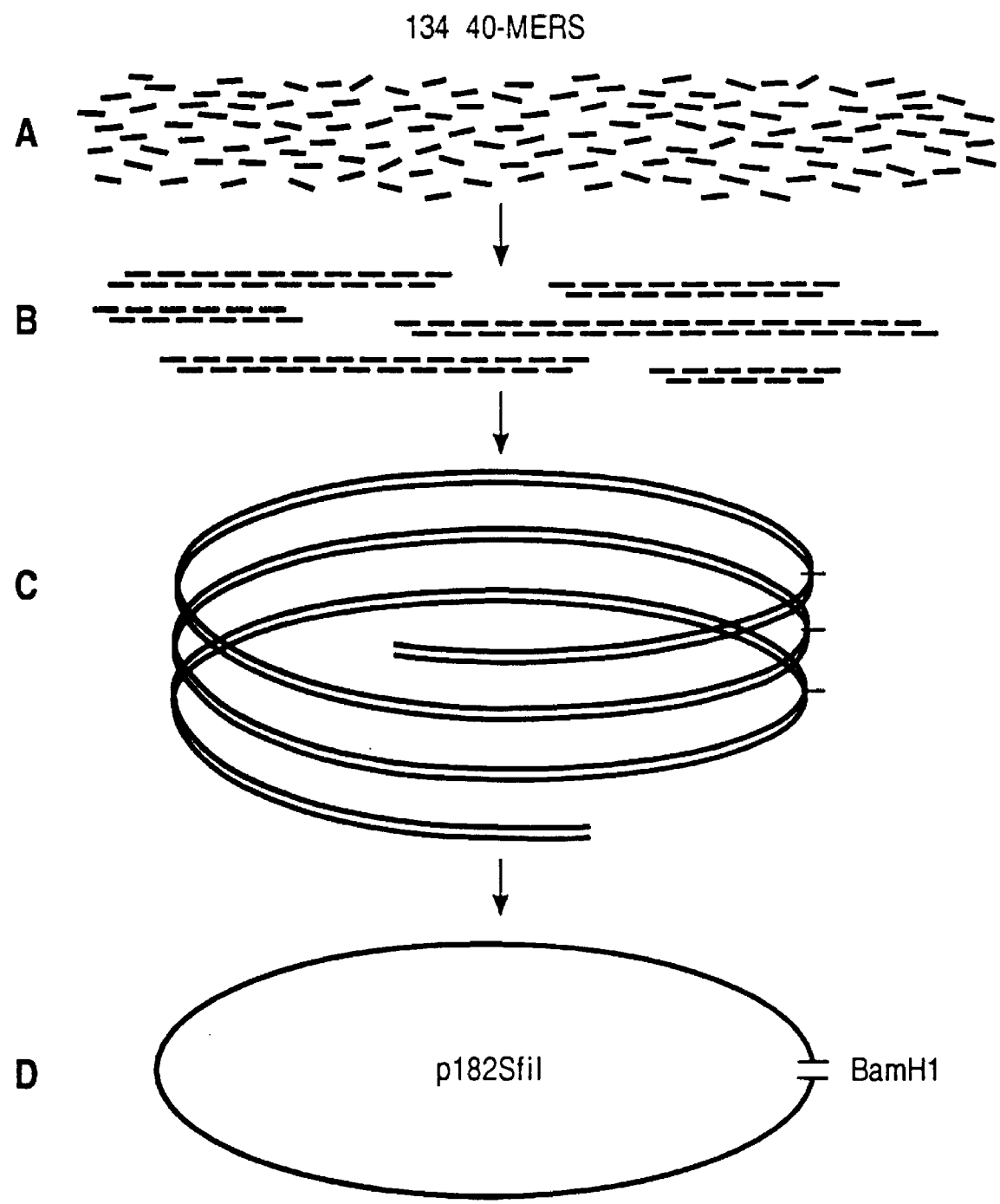
FIG. 6 Schematic of plasmid construction by overlapping fragment PCR as performed in Experimental Examples.

This example demonstrates assembly of a 2.71 kb plasmid p182SfiI (Stemmer (1994) Nature 370: 389) which encodes the gene and promoter region for R-TEM1 μ-lactamase. A collection of 132 component oligonucleotides, each 40 bases in length, as well as one 56-mer and one 47-mer (see, FIG. 5A–E) were synthesized and used to assemble the plasmid by end-complementary polymerase reaction (ECPR) employing the overlapping ends of the oligonucleotides. This collection of component polynucleotides collectively encode the plasmid p182SfiI. The plus strand and the minus strand were each initially directed by oligonucleotides 40 nucleotides long which, upon assembly, overlapped by 20 nucleotides (FIG. 6). The oligonucleotides were synthesized and 5'-phosphorylated simultaneously on a 96-well parallel-array DNA synthesizer using standard phosphoramidite chemistry. After cleavage from the solid support and deprotection, the dried down oligonucleotides were resuspended in distilled water and used without further purification.

Figure 7:
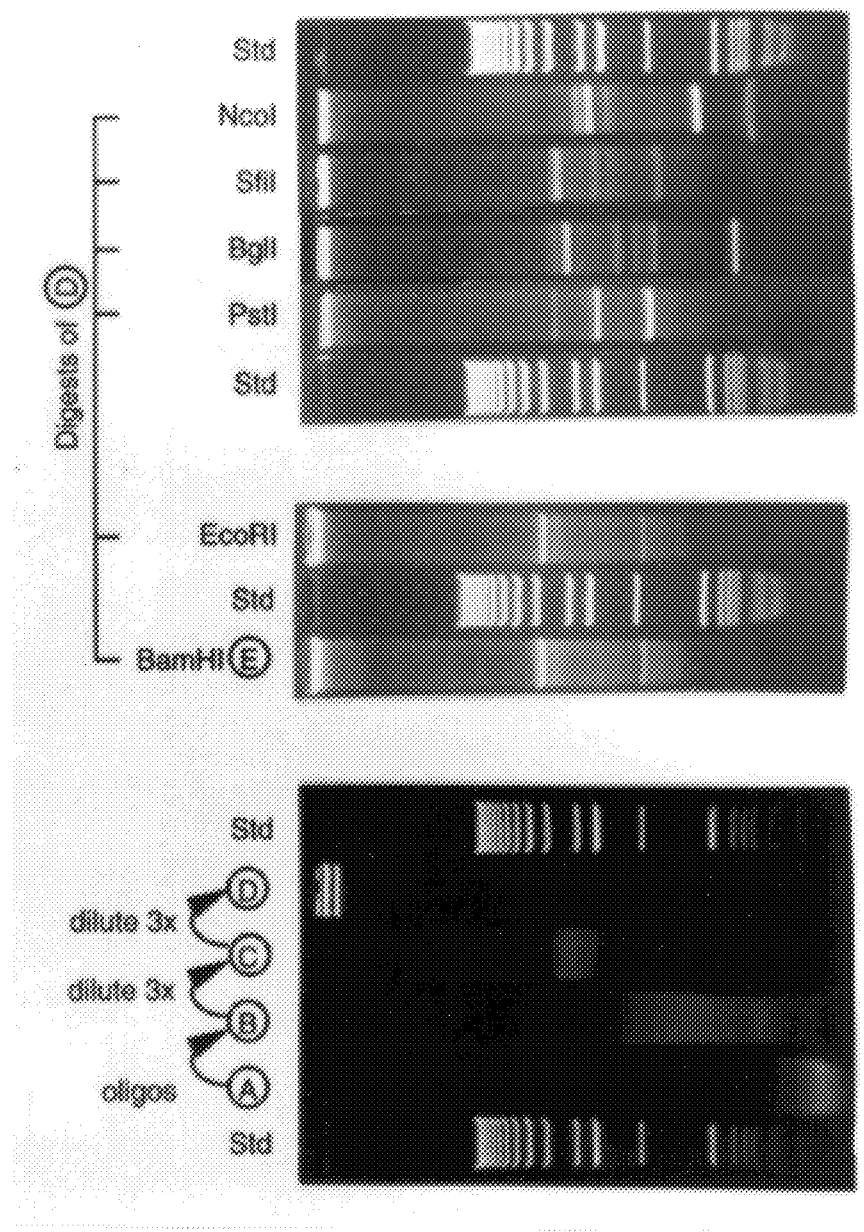
FIG. 7 Agarose gel electrophoresis of products generated during construction of the 2.7 kb circular plasmid p182SfiI by end-complementary polymerase reaction. The circled letters refer to aliquots removed from various amplification reactions: (A) is the mixture of oligonucleotides without polymerase, (B) is the product of the first set of amplification cycles, (C) is the product of the second set of amplification cycles, (D) is the final product.

The oligonucleotides were diluted to a final concentration (all oligos combined) of 1μM (14 ng/μl) in 20 μl of Gene-AMP XL PCR Mix (Perkin-Elmer, Branchburg, N.J.; 0.2mM each dNTP, 2.2 mM MgCl$_2$, 50 mM KCl, 10 mM Tris-HCl pH 9.0, 0.1% Triton X-100). An aliquot of the reaction mix (A) was electrophoresed on an agarose gel (FIG. 7). The reaction was started with 5 μl of a 50:1 (v/v) mixture of Taq polymerase (Promega, Madison, Wis.) and Pfu polymerase (Stratagene, La Jolla, Calif.) such that 1 unit of Taq and 0.02 unit of Pfu polymerase were added. The PCR program consisted of the following program: 40° C. for 2 minutes, 72° C. for 10 seconds, then 40 cycles of (94° C. for 15 seconds, 40° C. for 30 seconds, and 72° C. for [10 seconds + 1 second/cycle]). An aliquot of the resulting reaction product (B) was electrophoresed on an agarose gel (FIG. 7), the remainder was then diluted 3x with XL PCR Mix and enzyme and amplified with the following program: 25 cycles of (94° C. for 15 seconds, 40° C. for 30 seconds, and 72° C. for [45 seconds + 1 second/cycle]). An aliquot of the resulting reaction product (C) was electrophoresed on an agarose gel (FIG. 7) and the remainder then diluted 3x with XL PCR Mix and enzyme and amplified with the following program: 20 cycles of (94° C. for 15 seconds, 40° C. for 30 seconds, and 72° C. for [70 seconds + 1 second/cycle]). An aliquot of the resulting reaction product (D) was electrophoresed on an agarose gel (FIG. 7).

The an aliquot of the reaction product (D) was electrophoresed on an agarose gel, as was an aliquot which was digested with BamHI, which verified assembly of large DNA molecules consistent with formation of large concatemers which was resolved to unit length with BamHI digestion. The PCR product obtained by this method was shown to be concatemeric, and was resolvable by BamHI digestion into a single 2.7 kb band by agarose gel electrophoresis.

Aliquots of reaction product (D) were digested with various restriction enzymes (shown in FIG. 7). FIG. 7 shows that the unique cutters EcoRI and BamHI liberated a 2.71 kb fragment consistent with the size of a complete 2.71 kb plasmid p182SfiI (Stemmer (1994) Nature 370: 389, incorporated herein by reference). Furthermore, the digestion results with NcoI, SfiI, PstI, and BglII all yielded fragments consistent with the restriction map of the complete 2.71 kb plasmid p182SfiI.

After digestion of the PCR product with BamHI, the 2.7 kb fragment was gel purified and ligated with ligase, and transformed into E. coli. and transformed into E. coli K-12. Tetracycline-resistant transformants were selected.

This example demonstrates that the circular DNA assembly method allows for rapid and inexpensive construction of long DNA sequences, such as genes, gene libraries, plasmids, viral genomes, etc. The assembly method facilitates several mutagenesis approaches, such as point mutagenesis, combinatorial cassette mutagenesis, and doping, or mixing in other nucleotides during oligonucleotide synthesis. Deliberate modifications to the DNA sequence can be made simply by substituting one or more new oligos followed by reassembly. To reduce the rate of PCR mutagenesis during assembly, the addition of a proofreading polymerase can assure efficient long-read PCR reactions by combining high processivity with proofreading.

Example 3
Antibody Germline Assembly from Oligos With Rolling Circle Concatemeric Amplification A scFv antibody with germline sequences ($V_H251$ and $V_{IA}25$) was constructed from 19 oligonucleotides by cyclized assembly. The oligos were at 2–20 μg per μl in PCR Mix. the program was 20 cycles of (94° C. for 15s, 48° C. for 30s, 72° C. for 30+1s/cycle). The size of the product of this reaction was 200–500 bp. The PCR product was diluted 4-fold in PCR Mix and PCR was run for 24 cycles of (94° C. for 15s, 55° C. for 30s, 72° C. for 30+8s/cycle), followed by one additional 3-fold dilution and 20 cycles of (94° C. for 15s, 55° C. for 30s, 72° C. for 30+8s/cycle). The product was >50 kilobases, and after digestion with SfiI and NotI resulted in a single DNA fragment of the correct size.

FIG. 8 shows a schematic for end-complementary polymerase reaction (ECPR) in conjunction with parallel-processing PCR to amplify very large polynucleotides, such as those larger than can be amplified reliably by conventional PCR using only a single primer set.

Example 4
Plasmid Assembly With Rolling Circle Concatemeric Amplification pGJ103 is a 5.5 kilobase plasmid containing an intact ars operon (Ji and Silver (1992) *Proc. Natl. Acad. Sci.* (*USA*) 89: 9474). pGJ103 was digested with DNAseI into random 100–400 bp fragments which were reassembled by circular shuffling in PCR Mix with a program of 50 cycles of (94° C. for 15ss, 68° C. for 30s+8s/cycle), using three different concentrations of fragments. Each reassembly yielded a product of >50 kb which was digested with BamHI to yield a single band of the correct (predicted) size, which was ligated, transformed into *E. coli*, and preplated on increasing levels of arsenate to select for up-mutants.

Although the present invention has been described in some detail by way of illustration for purposes of clarity of understanding, it will be apparent that certain changes and modifications may be practiced within the scope of the claims.

---

We claim:

1. A method for amplifying a target polynucleotide, comprising:

contacting under conditions suitable for PCR, target polynucleotide with a bivalent primer which comprises two portions of complementarity to the target polynucleotide: (1) a first portion which is in the 5' portion of the primer and which is substantially complementary to a sequence in the 5' portion of the sequence to be amplified (target sequence) in the target polynucleotide, and (2) a second portion which is in the 3' portion of the primer and which is substantially complementary to a sequence in the 3' portion of the sequence to be amplified (target sequence) in the target polynucleotide;

catalyzing under suitable reaction conditions for PCR, polynucleotide synthesis primed from the 3'-hydroxyl of the annealed bivalent primer to form a strand complementary to the target sequence, thereby forming a nascent complementary strand;

denaturing the target polynucleotide and the nascent strand and allowing reannealing, under dilute conditions suitable for substantial intramolecular annealing and circle formation, the nascent strand with a complementary strand of a target polynucleotide or an amplified copy thereof to form amplification intermediates in the form of cyclized DNA as a result of the 3' terminus of an overlapped nascent strand annealing to the 3' terminus of an overlapped complementary strand which has a strand with an extendable 3'-hydroxyl which can be extended with a DNA polymerase substantially lacking exonuclease activity whereby the leading terminus of the nascent strand continually displaces the lagging portion of the nascent strand producing a concatemeric single strand emanating from the amplification intermediate; and repeating an elongation/denaturation/reannealing cycle from 1 to about 100 times as desired, resulting in formation of amplified product which comprises head-to-tail concatemers of the target sequence.

2. The method of claim 1, comprising the further step of cleaving said concatemers with a restriction endonuclease which cuts within each concatemeric unit to form a population of polynucleotides each consisting of an amplified target sequence.

3. The method of claim 2, comprising the further step of ligating the population of polynucleotides each consisting of an amplified target sequence with DNA ligase to form covalently closed circles.

4. The method of claim 2, comprising the further step of ligating the population of polynucleotides each consisting of an amplified target sequence by direct transformation into host cells for in vivo ligation.

5. The method of claim 1, wherein said polynucleotide synthesis primed from the 3'-hydroxyl of the annealed primer forms a sequence-variant of the strand complementary to the target sequence.

6. The method of claim 5, wherein repeating said elongation/denaturation/reannealing cycle from 1 to about 100 times, results in a library which comprises a plurality of sequence-variants of the strand complementary to the target sequence.

7. A method of forming a polynucleotide, comprising:
   (1) providing two double-stranded polynucleotides overlapping at both ends, which can be denatured to single-stranded polynucleotides having complementary ends that can anneal to generate a circular form;
   (2) denaturing the double-stranded polynucleotides to generate the single-stranded polynucleotides;
   (3) incubating the single-stranded polynucleotides under conditions whereby complementary ends anneal;
   (4) extending the 3' ends of annealed polynucleotides, under conditions whereby each polynucleotide serves as a template for another;
   (5) repeating steps (2)–(4) 1–100 times, whereby the extended polynucleotides in step (4) constitute the double-stranded polynucleotides in step (2) in the next cycle.

8. The method of claim 7, wherein one of the double stranded polynucleotides includes a variable-sequence kernel.

* * * * *

UNITED STATES PATENT AND TRADEMARK OFFICE
CERTIFICATE OF CORRECTION

PATENT NO. : 5,834,252

DATED : November 10, 1998

INVENTOR(S) : Willem P.C. Stemmer et al.

It is certified that error appears in the above-identified patent and that said Letters Patent is hereby corrected as shown below:

In the cover page, designation of Assignee, please add <u>Affymetrix, Inc., Santa Clara, California</u> as a co-assignee as shown below.

Assignees:

Glaxo Group Limited
Middlesex, England

Affymetrix, Inc.
Santa Clara, California

Signed and Sealed this

Thirty-first Day of October, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 136

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

A A A G C G T C G A     T T T T T G T G A T                                                        2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

A T G G G G T T C C     G C G C A C A T T T                                                        2 0

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:3:

C T C A C G T T A A     G G G A T T T T G G     T C A T G A G A T T     A T C A A A A A G G           4 0

( 2 ) INFORMATION FOR SEQ ID NO:4:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:4:

ATCTTCACCT AGATCCTTTT AAATTAAAAA TGAAGTTTTA 40

( 2 ) INFORMATION FOR SEQ ID NO:5:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: circular ( x i ) SEQUENCE DESCRIPTION: SEQ ID NO:5:

AATCAATCTA AAGTATATAT GAGGCCTGAC AGGCCGGTCT 40

( 2 ) INFORMATION FOR SEQ ID NO:6:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:6:

GACAGTTACC AATGCTTAAT CAGTGAGGCA CCTATCTCAG 40

( 2 ) INFORMATION FOR SEQ ID NO:7:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:7:

CGATCTGTCT ATTTCGTTCA TCCATGGTTG CCTGACTCCC 40

( 2 ) INFORMATION FOR SEQ ID NO:8:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:8:

CGTCGTGTAG ATAACTACGA TACGGGAGGG CTTACCATCT 40

( 2 ) INFORMATION FOR SEQ ID NO:9:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:9:

GGCCCCAGTG CTGCAATGAT ACCGCGAGAC CCACGCTCAC 40

( 2 ) INFORMATION FOR SEQ ID NO:10:

( i ) SEQUENCE CHARACTERISTICS:
    ( A ) LENGTH: 40 base pairs (B) TYPE: nucleic acid
(C) STRANDEDNESS: double
(D) TOPOLOGY: circular (xi) SEQUENCE DESCRIPTION: SEQ ID NO:10:

CGGCTCCAGA TTTATCAGCA ATAAACCAGC CAGCTGGAAG 40

(2) INFORMATION FOR SEQ ID NO:11:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:11:

GGCCGAGCGC AGAAGTGGTC CTGCAACTTT ATCCGCCTCC 40

(2) INFORMATION FOR SEQ ID NO:12:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:12:

ATCCAGTCTA TTAATTGTTG CCGGGAAGCT AGAGTAAGTA 40

(2) INFORMATION FOR SEQ ID NO:13:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:13:

GTTCGCCAGT TAATAGTTTG CGCAACGTTG TTGCCATGGC 40

(2) INFORMATION FOR SEQ ID NO:14:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:14:

TACAGGCATC GTGGTGTCAC GCTCGTCGTT TGGAATGGCT 40

(2) INFORMATION FOR SEQ ID NO:15:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:15:

TCATTCAGCT CCGGTTCCCA ACGATCAAGG CGAGTTACAT 40

(2) INFORMATION FOR SEQ ID NO:16:

(i) SEQUENCE CHARACTERISTICS:
(A) LENGTH: 40 base pairs
(B) TYPE: nucleic acid
(C) STRANDEDNESS: double (D) TOPOLOGY: circular (x i) SEQUENCE DESCRIPTION: SEQ ID NO:16:

GATCCCCCAT GTTGTGCAAA AAAGCGGTTA GCTCCTTCGG 40

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:17:

TCCTCCGATG CTTGTCAGAA GTAAGTTGGC TGCAGTGTTA 40

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:18:

TCACTCATGG TTATGGCAGC ACTGCATAAT TCTCTTACTG 40

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:19:

TCATGCCATC CGTAAGATGC TTTTCTGTGA CTGGTGAGTA 40

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:20:

CTCAACCAAG TCATTCTGAG AATAGTGTAT GCGGCGACCG 40

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:21:

AGTTGCTCTT GCCCGGCGTC AATACGGGAT AATACCGCGC 40

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:22:

CACATAGCAG AACTTTAAAA GTGCTCATCA TTGGAAAACG                40

(2) INFORMATION FOR SEQ ID NO:23:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:23:

TTCTTCGGGG CGAAAACTCT CAAGGATCTT ACCGCTGTTG                40

(2) INFORMATION FOR SEQ ID NO:24:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:24:

AGATCCAGTT CGATGTAACC CACTCGTGCA CCCAACTGAT                40

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:25:

CTTCAGCATC TTTTACTTTC ACCAGCGTTT CTGGGTGAGC                40

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:26:

AAAAACAGGA AGGCAAAATG CCGCAAAAAA GGGAATAAGG                40

(2) INFORMATION FOR SEQ ID NO:27:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:27:

GCGACACGGA AATGTTGAAT ACTCATACTC TTCCTTTTTC                40

(2) INFORMATION FOR SEQ ID NO:28:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:28:

AATATTATTG AAGCATTTAT CAGGGTTATT GTCTCATGAG 40

( 2 ) INFORMATION FOR SEQ ID NO:29:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:29:

CGGATACATA TTTGAATGTA TTTAGGCCAT GGTGGCCAAA 40

( 2 ) INFORMATION FOR SEQ ID NO:30:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:30:

AATAAACAAA TAGGGGTTCC GCGCACATTT CCCCGAAAAG 40

( 2 ) INFORMATION FOR SEQ ID NO:31:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:31:

TTCTTAGACG TCAGGTGGCA CTTTTCGGGG AAATGTGCGC 40

( 2 ) INFORMATION FOR SEQ ID NO:32:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:32:

GGAACCCCTA TTTGTTTATT TTTGGCCACC ATGGCCTAAA 40

( 2 ) INFORMATION FOR SEQ ID NO:33:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:33:

TACATTCAAA TATGTATCCG CTCATGAGAC AATAACCTG 40

( 2 ) INFORMATION FOR SEQ ID NO:34:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:34:

ATAAATGCTT CAATAATATT GAAAAGGAA GAGTATGAGT 40

( 2 ) INFORMATION FOR SEQ ID NO:35:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:35:

ATTCAACATT TCCGTGTCGC CCTTATTCCC TTTTTTGCGG    40

( 2 ) INFORMATION FOR SEQ ID NO:36:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:36:

CATTTTGCCT TCCTGTTTTT GCTCACCCAG AAACGCTGGT    40

( 2 ) INFORMATION FOR SEQ ID NO:37:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:37:

GAAAGTAAAA GATGCTGAAG ATCAGTTGGG TGCACGAGTG    40

( 2 ) INFORMATION FOR SEQ ID NO:38:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:38:

GGTTACATCG AACTGGATCT CAACAGCGGT AAGATCCTTG    40

( 2 ) INFORMATION FOR SEQ ID NO:39:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:39:

AGAGTTTTCG CCCCGAAGAA CGTTTTCCAA TGATGAGCAC    40

( 2 ) INFORMATION FOR SEQ ID NO:40:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:40:

TTTTAAAGTT CTGCTATGTG GCGCGGTATT ATCCCGTATT    40

( 2 ) INFORMATION FOR SEQ ID NO:41:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:41:

GACGCCGGGC AAGAGCAACT CGGTCGCCGC ATACACTATT    40

( 2 ) INFORMATION FOR SEQ ID NO:42:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:42:

CTCAGAATGA CTTGGTTGAG TACTCACCAG TCACAGAAAA    40

( 2 ) INFORMATION FOR SEQ ID NO:43:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:43:

GCATCTTACG GATGGCATGA CAGTAAGAGA ATTATGCAGT    40

( 2 ) INFORMATION FOR SEQ ID NO:44:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:44:

GCTGCCATAA CCATGAGTGA TAACACTGCA GCCAACTTAC    40

( 2 ) INFORMATION FOR SEQ ID NO:45:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:45:

TTCTGACAAC GATCGGAGGA CCGAAGGAGC TAACCGCTTT    40

( 2 ) INFORMATION FOR SEQ ID NO:46:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:46:

TTTGCACAAC ATGGGGATC ATGTAACTCG CCTTGATCGT    40

( 2 ) INFORMATION FOR SEQ ID NO:47:

( i ) SEQUENCE CHARACTERISTICS:

( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:47:

TGGGAACCGG AGCTGAATGA AGCCATTCCA AACGACGAGC  40

( 2 ) INFORMATION FOR SEQ ID NO:48:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:48:

GTGACACCAC GATGCCTGTA GCCATGGCAA CAACGTTGCG  40

( 2 ) INFORMATION FOR SEQ ID NO:49:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:49:

CAAACTATTA ACTGGCGAAC TACTTACTCT AGCTTCCCGG  40

( 2 ) INFORMATION FOR SEQ ID NO:50:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:50:

CAACAATTAA TAGACTGGAT GGAGGCGGAT AAAGTTGCAG  40

( 2 ) INFORMATION FOR SEQ ID NO:51:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:51:

GACCACTTCT GCGCTCGGCC CTTCCAGCTG GCTGGTTTAT  40

( 2 ) INFORMATION FOR SEQ ID NO:52:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:52:

TGCTGATAAA TCTGGAGCCG GTGAGCGTGG GTCTCGCGGT  40

( 2 ) INFORMATION FOR SEQ ID NO:53:

( i ) SEQUENCE CHARACTERISTICS:
( A ) LENGTH: 40 base pairs
( B ) TYPE: nucleic acid 5,834,252

39

40

-continued ( C ) STRANDEDNESS: double
( D ) TOPOLOGY: circular ( x i ) SEQUENCE DESCRIPTION: SEQ ID NO:53:

ATCATTGCAG CACTGGGGCC AGATGGTAAG CCCTCCCGTA     40

( 2 ) INFORMATION FOR SEQ ID NO:54:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:54:

TCGTAGTTAT CTACACGACG GGGAGTCAGG CAACCATGGA     40

( 2 ) INFORMATION FOR SEQ ID NO:55:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:55:

TGAACGAAAT AGACAGATCG CTGAGATAGG TGCCTCACTG     40

( 2 ) INFORMATION FOR SEQ ID NO:56:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:56:

ATTAAGCATT GGTAACTGTC AGACCGGCCT GTCAGGCCTC     40

( 2 ) INFORMATION FOR SEQ ID NO:57:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:57:

ATATATACTT TAGATTGATT TAAAACTTCA TTTTTAATTT     40

( 2 ) INFORMATION FOR SEQ ID NO:58:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:58:

AAAAGGATCT AGGTGAAGAT CCTTTTTGAT AATCTCATGA     40

( 2 ) INFORMATION FOR SEQ ID NO:59:

( i ) SEQUENCE CHARACTERISTICS:
( A ) LENGTH: 40 base pairs
( B ) TYPE: nucleic acid
( C ) STRANDEDNESS: double
( D ) TOPOLOGY: circular ( x i ) SEQUENCE DESCRIPTION: SEQ ID NO:59:

GGAAAACCCT GGCGTTACCC AACTTAATCG CCTTGCAGCA          40

( 2 ) INFORMATION FOR SEQ ID NO:60:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:60:

CATCCCCTT TCGCCAGCTG GCGTAATAGC GAAGAGGCCC          40

( 2 ) INFORMATION FOR SEQ ID NO:61:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:61:

GCACCGATCG CCCTTCCCAA CAGTTGCGTA GCCTGAATGG          40

( 2 ) INFORMATION FOR SEQ ID NO:62:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:62:

CGAATGGCGC CTGATGCGGT ATTTTCTCCT TACGCATCTG          40

( 2 ) INFORMATION FOR SEQ ID NO:63:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:63:

TGCGGTATTT CACACCGCAT ATGGTGCACT CTCAGTACAA          40

( 2 ) INFORMATION FOR SEQ ID NO:64:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:64:

TCTGCTCTGA TGCCGCATAG TTAAGCCAGC CCCGACACCC          40

( 2 ) INFORMATION FOR SEQ ID NO:65:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:65:

GCCAACACCC GCTGACGCGC CCTGACGGGC TTGTCTGCTC        40

( 2 ) INFORMATION FOR SEQ ID NO:66:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:66:

CCGGCATCCG CTTACAGACA AGCTGTGACC GTCTCCGGGA        40

( 2 ) INFORMATION FOR SEQ ID NO:67:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:67:

GCTGCATGTG TCAGAGGTTT TCACCGTCAT CACCGAAACG        40

( 2 ) INFORMATION FOR SEQ ID NO:68:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:68:

CGAGGCCCTT TCGTCTCGCG CGTTTCGGTG ATGACGGTGA        40

( 2 ) INFORMATION FOR SEQ ID NO:69:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:69:

AAACCTCTGA CACATGCAGC TCCCGGAGAC GGTCACAGCT        40

( 2 ) INFORMATION FOR SEQ ID NO:70:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:70:

TGTCTGTAAG CGGATGCCGG GAGCAGACAA GCCCGTCAGG        40

( 2 ) INFORMATION FOR SEQ ID NO:71:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:71:

GCGCGTCAGC GGGTGTTGGC GGGTGTCGGG GCTGGCTTAA        40

( 2 ) INFORMATION FOR SEQ ID NO:72:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:72:

CTATGCGGCA TCAGAGCAGA TTGTACTGAG AGTGCACCAT    40

( 2 ) INFORMATION FOR SEQ ID NO:73:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:73:

ATGCGGTGTG AAATACCGCA CAGATGCGTA AGGAGAAAAT    40

( 2 ) INFORMATION FOR SEQ ID NO:74:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:74:

ACCGCATCAG GCGCCATTCG CCATTCAGGC TACGCAACTG    40

( 2 ) INFORMATION FOR SEQ ID NO:75:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:75:

TTGGGAAGGG CGATCGGTGC GGGCCTCTTC GCTATTACGC    40

( 2 ) INFORMATION FOR SEQ ID NO:76:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:76:

CAGCTGGCGA AAGGGGATG TGCTGCAAGG CGATTAAGTT    40

( 2 ) INFORMATION FOR SEQ ID NO:77:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:77:

GGGTAACGCC AGGGTTTTCC CAGTCACGAC GTTGTAAAAC    40

( 2 ) INFORMATION FOR SEQ ID NO:78:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:78:

GACGGCCAGT GCCAAGCTTG CATGCCTGCA GGTCGACTCT 40

( 2 ) INFORMATION FOR SEQ ID NO:79:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:79:

AGAGGATCCC CGGGTACCGA GCTCGAATTC GTAATCATGG 40

( 2 ) INFORMATION FOR SEQ ID NO:80:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:80:

TCATAGCTGT TTCCTGTGTG AAATTGTTAT CCGCTCACAA 40

( 2 ) INFORMATION FOR SEQ ID NO:81:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:81:

TTCCACACAA CATACGAGCC GGAAGCATAA AGTGTAAAGC 40

( 2 ) INFORMATION FOR SEQ ID NO:82:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:82:

CTGGGGTGCC TAATGAGTGA GCTAACTCAC ATTAATTGCG 40

( 2 ) INFORMATION FOR SEQ ID NO:83:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:83:

TTGCGCTCAC TGCCCGCTTT CCAGTCGGGA AACCTGTCGT 40

( 2 ) INFORMATION FOR SEQ ID NO:84:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:84:

GCCAGCTGCA TTAATGAATC GGCCAACGCG CGGGGAGAGG 40

( 2 ) INFORMATION FOR SEQ ID NO:85:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:85:

CGGTTTGCGT ATTGGGCGCT CTTCCGCTTC CTCGCTCACT 40

( 2 ) INFORMATION FOR SEQ ID NO:86:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:86:

GACTCGCTGC GCTCGGTCGT TCGGCTGCGG CGAGCGGTAT 40

( 2 ) INFORMATION FOR SEQ ID NO:87:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:87:

CAGCTCACTC AAAGGCGGTA ATACGGTTAT CCACAGAATC 40

( 2 ) INFORMATION FOR SEQ ID NO:88:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:88:

AGGGGATAAC GCAGGAAAGA ACATGTGAGC AAAAGGCCAG 40

( 2 ) INFORMATION FOR SEQ ID NO:89:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:89:

CAAAAGGCCA GGAACCGTAA AAAGGCCGCG TTGCTGGCGT 40

( 2 ) INFORMATION FOR SEQ ID NO:90:

( i ) SEQUENCE CHARACTERISTICS:
    ( A ) LENGTH: 40 base pairs (B) TYPE: nucleic acid
(C) STRANDEDNESS: double
(D) TOPOLOGY: circular (xi) SEQUENCE DESCRIPTION: SEQ ID NO:90:

TTTTCCATAG GCTCCGCCCC CCTGACGAGC ATCACAAAAA         40

(2) INFORMATION FOR SEQ ID NO:91:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:91:

TCGACGCTCA AGTCAGAGGT GGCGAAACCC GACAGGACTA         40

(2) INFORMATION FOR SEQ ID NO:92:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:92:

TAAAGATACC AGGCGTTTCC CCCTGGAAGC TCCCTCGTGC         40

(2) INFORMATION FOR SEQ ID NO:93:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:93:

GCTCTCCTGT TCCGACCCTG CCGCTTACCG GATACCTGTC         40

(2) INFORMATION FOR SEQ ID NO:94:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:94:

CGCCTTTCTC CCTTCGGGAA GCGTGGCGCT TTCTCAATGC         40

(2) INFORMATION FOR SEQ ID NO:95:

(i) SEQUENCE CHARACTERISTICS:
(A) LENGTH: 40 base pairs
(B) TYPE: nucleic acid
(C) STRANDEDNESS: double
(D) TOPOLOGY: circular (xi) SEQUENCE DESCRIPTION: SEQ ID NO:95:

TCACGCTGTA GGTATCTCAG TTCGGTGTAG GTCGTTCGCT         40

(2) INFORMATION FOR SEQ ID NO:96:

(i) SEQUENCE CHARACTERISTICS:
(A) LENGTH: 40 base pairs
(B) TYPE: nucleic acid
(C) STRANDEDNESS: double (D) TOPOLOGY: circular (x i) SEQUENCE DESCRIPTION: SEQ ID NO:96:

CCAAGCTGGG CTGTGTGCAC GAACCCCCCG TTCAGCCCGA 40

(2) INFORMATION FOR SEQ ID NO:97:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:97:

CCGCTGCGCC TTATCCGGTA ACTATCGTCT TGAGTCCAAC 40

(2) INFORMATION FOR SEQ ID NO:98:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:98:

CCGGTAAGAC ACGACTTATC GCCACTGGCA GCAGCCACTG 40

(2) INFORMATION FOR SEQ ID NO:99:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:99:

GTAACAGGAT TAGCAGAGCG AGGTATGTAG GCGGTGCTAC 40

(2) INFORMATION FOR SEQ ID NO:100:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:100:

AGAGTTCTTG AAGTGGTGGC CTAACTACGG CTACACTAGA 40

(2) INFORMATION FOR SEQ ID NO:101:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (x i) SEQUENCE DESCRIPTION: SEQ ID NO:101:

AGGACAGTAT TTGGTATCTG CGCTCTGCTG AAGCCAGTTA 40

(2) INFORMATION FOR SEQ ID NO:102:

(i) SEQUENCE CHARACTERISTICS:
        (A) LENGTH: 40 base pairs
        (B) TYPE: nucleic acid
        (C) STRANDEDNESS: double
        (D) TOPOLOGY: circular ( x i ) SEQUENCE DESCRIPTION: SEQ ID NO:102:

CCTTCGGAAA AAGAGTTGGT AGCTCTTGAT CCGGCAAACA 40

( 2 ) INFORMATION FOR SEQ ID NO:103:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:103:

AACCACCGCT GGTAGCGGTG GTTTTTTTGT TTGCAAGCAG 40

( 2 ) INFORMATION FOR SEQ ID NO:104:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:104:

CAGATTACGC GCAGAAAAAA AGGATCTCAA GAAGATCCTT 40

( 2 ) INFORMATION FOR SEQ ID NO:105:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:105:

TGATCTTTTC TACGGGGTCT GACGCTCAGT GGAACGAAAA 40

( 2 ) INFORMATION FOR SEQ ID NO:106:

( i ) SEQUENCE CHARACTERISTICS:
        ( A ) LENGTH: 56 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:106:

CGCGAGACGA AAGGGCCTCG TGATACGCCT ATTTTTATAG GTTAATGTCA TGATAA 56

( 2 ) INFORMATION FOR SEQ ID NO:107:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:107:

TGCCACCTGA CGTCTAAGAA ACCATTATTA TCATGACATT AACCTAT 47

( 2 ) INFORMATION FOR SEQ ID NO:108:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:108:

CCAAAATCCC TTAACGTGAG TTTTCGTTCC ACTGAGCGTC                40

( 2 ) INFORMATION FOR SEQ ID NO:109:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:109:

AGACCCGTA GAAAAGATCA AAGGATCTTC TTGAGATCCT                40

( 2 ) INFORMATION FOR SEQ ID NO:110:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:110:

TTTTTTCTGC GCGTAATCTG CTGCTTGCAA ACAAAAAAAC                40

( 2 ) INFORMATION FOR SEQ ID NO:111:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:111:

CACCGCTACC AGCGGTGGTT TGTTTGCCGG ATCAAGAGCT                40

( 2 ) INFORMATION FOR SEQ ID NO:112:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:112:

ACCAACTCTT TTTCCGAAGG TAACTGGCTT CAGCAGAGCG                40

( 2 ) INFORMATION FOR SEQ ID NO:113:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:113:

CAGATACCAA ATACTGTCCT TCTAGTGTAG CCGTAGTTAG                40

( 2 ) INFORMATION FOR SEQ ID NO:114:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:114:

GCCACCACTT CAAGAACTCT GTAGCACCGC CTACATACCT                40

( 2 ) INFORMATION FOR SEQ ID NO:115:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:115:

CGCTCTGCTA ATCCTGTTAC CAGTGGCTGC TGCCAGTGGC    40

( 2 ) INFORMATION FOR SEQ ID NO:116:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:116:

GATAAGTCGT GTCTTACCGG GTTGGACTCA AGACGATAGT    40

( 2 ) INFORMATION FOR SEQ ID NO:117:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:117:

TACCGGATAA GGCGCAGCGG TCGGGCTGAA CGGGGGGTTC    40

( 2 ) INFORMATION FOR SEQ ID NO:118:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:118:

GTGCACACAG CCCAGCTTGG AGCGAACGAC CTACACCGAA    40

( 2 ) INFORMATION FOR SEQ ID NO:119:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:119:

CTGAGATACC TACAGCGTGA GCATTGAGAA AGCGCCACGC    40

( 2 ) INFORMATION FOR SEQ ID NO:120:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:120:

TTCCCGAAGG GAGAAAGGCG GACAGGTATC CGGTAAGCGG    40

( 2 ) INFORMATION FOR SEQ ID NO:121:

( i ) SEQUENCE CHARACTERISTICS:
  ( A ) LENGTH: 40 base pairs
  ( B ) TYPE: nucleic acid
  ( C ) STRANDEDNESS: double
  ( D ) TOPOLOGY: circular ( x i ) SEQUENCE DESCRIPTION: SEQ ID NO:121:

CAGGGTCGGA ACAGGAGAGC GCACGAGGGA GCTTCCAGGG      40

( 2 ) INFORMATION FOR SEQ ID NO:122:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:122:

GGAAACGCCT GGTATCTTTA TAGTCCTGTC GGGTTTCGCC      40

( 2 ) INFORMATION FOR SEQ ID NO:123:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:123:

ACCTCTGACT TGAGCGTCGA TTTTTGTGAT GCTCGTCAGG      40

( 2 ) INFORMATION FOR SEQ ID NO:124:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:124:

GGGGCGGAGC CTATGGAAAA ACGCCAGCAA CGCGGCCTTT      40

( 2 ) INFORMATION FOR SEQ ID NO:125:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:125:

TTACGGTTCC TGGCCTTTTG CTGGCCTTTT GCTCACATGT      40

( 2 ) INFORMATION FOR SEQ ID NO:126:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: circular ( x i ) SEQUENCE DESCRIPTION: SEQ ID NO:126:

TCTTTCCTGC GTTATCCCCT GATTCTGTGG ATAACCGTAT      40

( 2 ) INFORMATION FOR SEQ ID NO:127:

( i ) SEQUENCE CHARACTERISTICS:

(A) LENGTH: 40 base pairs
    (B) TYPE: nucleic acid
    (C) STRANDEDNESS: double
    (D) TOPOLOGY: circular (xi) SEQUENCE DESCRIPTION: SEQ ID NO:127:

TACCGCCTTT GAGTGAGCTG ATACCGCTCG CCGCAGCCGA                                40

(2) INFORMATION FOR SEQ ID NO:128:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:128:

ACGACCGAGC GCAGCGAGTC AGTGAGCGAG GAAGCGGAAG                                40

(2) INFORMATION FOR SEQ ID NO:129:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:129:

AGCGCCCAAT ACGCAAACCG CCTCTCCCCG CGCGTTGGCC                                40

(2) INFORMATION FOR SEQ ID NO:130:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:130:

GATTCATTAA TGCAGCTGGC ACGACAGGTT TCCCGACTGG                                40

(2) INFORMATION FOR SEQ ID NO:131:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:131:

AAAGCGGGCA GTGAGCGCAA CGCAATTAAT GTGAGTTAGC                                40

(2) INFORMATION FOR SEQ ID NO:132:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:132:

TCACTCATTA GGCACCCCAG GCTTTACACT TTATGCTTCC                                40

(2) INFORMATION FOR SEQ ID NO:133:

(i) SEQUENCE CHARACTERISTICS:
        (A) LENGTH: 40 base pairs
        (B) TYPE: nucleic acid -continued (C) STRANDEDNESS: double
(D) TOPOLOGY: circular (xi) SEQUENCE DESCRIPTION: SEQ ID NO:133:

GGCTCGTATG TTGTGTGGAA TTGTGAGCGG ATAACAATTT                    40

(2) INFORMATION FOR SEQ ID NO:134:

(i) SEQUENCE CHARACTERISTICS:
    (A) LENGTH: 40 base pairs
    (B) TYPE: nucleic acid
    (C) STRANDEDNESS: double
    (D) TOPOLOGY: circular (xi) SEQUENCE DESCRIPTION: SEQ ID NO:134:

CACACAGGAA ACAGCTATGA CCATGATTAC GAATTCGAGC                    40

(2) INFORMATION FOR SEQ ID NO:135:

(i) SEQUENCE CHARACTERISTICS:
    (A) LENGTH: 40 base pairs
    (B) TYPE: nucleic acid
    (C) STRANDEDNESS: double
    (D) TOPOLOGY: circular (xi) SEQUENCE DESCRIPTION: SEQ ID NO:135:

TCGGTACCCG GGGATCCTCT AGAGTCGACC TGCAGGCATG                    40

(2) INFORMATION FOR SEQ ID NO:136:

(i) SEQUENCE CHARACTERISTICS:
    (A) LENGTH: 40 base pairs
    (B) TYPE: nucleic acid
    (C) STRANDEDNESS: double
    (D) TOPOLOGY: circular (xi) SEQUENCE DESCRIPTION: SEQ ID NO:136:

CAAGCTTGGC ACTGGCCGTC GTTTTACAAC GTCGTGACTG                    40